United States Patent [19]
Sy

[11] Patent Number: 5,879,951
[45] Date of Patent: Mar. 9, 1999

[54] OPPOSABLE-ELEMENT ASSAY DEVICE EMPLOYING UNIDIRECTIONAL FLOW

[75] Inventor: Vincent A. Sy, Cumberland Centre, Me.

[73] Assignee: SmithKline Diagnostics, inc., Palo Alto, Calif.

[21] Appl. No.: 791,769

[22] Filed: Jan. 29, 1997

[51] Int. Cl.⁶ ................................................. G01N 33/558
[52] U.S. Cl. ............................ 436/514; 422/56; 422/57; 422/58; 422/61; 435/7.9; 435/7.92; 435/287.1; 435/287.2; 435/287.7; 435/287.8; 435/287.9; 435/805; 435/810; 435/970; 435/975; 436/518; 436/528; 436/530; 436/169; 436/805; 436/808; 436/810
[58] Field of Search ................................. 422/56–58, 61; 435/7.9, 7.92, 287.1, 287.2, 287.7, 287.8, 287.9, 805, 810, 970, 975; 436/514, 518, 528, 530, 169, 805, 808, 810

[56] References Cited

U.S. PATENT DOCUMENTS

| | | |
|---|---|---|
| Re. 30,267 | 5/1980 | Bruschi . |
| Re. 31,006 | 8/1982 | Schuurs et al. . |
| Re. 35,306 | 7/1996 | Chen et al. . |
| 3,511,608 | 5/1970 | Anderson . |
| 3,620,677 | 11/1971 | Morison . |
| 3,644,177 | 2/1972 | Zyk . |
| 3,720,760 | 3/1973 | Bennich et al. . |
| 3,723,064 | 3/1973 | Liotta . |
| 3,785,930 | 1/1974 | Ellis . |
| 3,798,004 | 3/1974 | Zerachia et al. . |
| 3,888,629 | 6/1975 | Bagshawe . |
| 3,893,808 | 7/1975 | Campbell . |
| 3,901,657 | 8/1975 | Lightfoot . |
| 3,915,647 | 10/1975 | Wright . |
| 3,933,594 | 1/1976 | Milligan et al. . |
| 3,990,850 | 11/1976 | Friedman et al. . |
| 3,992,158 | 11/1976 | Przyblowicz et al. . |
| 4,012,198 | 3/1977 | Finter et al. . |
| 4,018,662 | 4/1977 | Ruhenstroth-Bauer et al. . |

(List continued on next page.)

FOREIGN PATENT DOCUMENTS

| | | |
|---|---|---|
| 0063810 | 11/1982 | European Pat. Off. . |
| 0093595 | 11/1983 | European Pat. Off. . |
| 0125118 | 11/1984 | European Pat. Off. . |
| 0154749 | 9/1985 | European Pat. Off. . |
| 0170746 | 2/1986 | European Pat. Off. . |
| 0183442 | 6/1986 | European Pat. Off. . |
| 0191640 | 8/1986 | European Pat. Off. . |
| 0204579 | 12/1986 | European Pat. Off. . |
| 0217403 | 4/1987 | European Pat. Off. . |
| 0225054 | 6/1987 | European Pat. Off. . |
| 0227173 | 7/1987 | European Pat. Off. . |
| 0238012 | 9/1987 | European Pat. Off. . |
| 0250137 | 12/1987 | European Pat. Off. . |
| 0253579 | 1/1988 | European Pat. Off. . |
| 0262328 | 4/1988 | European Pat. Off. . |
| 0267724 | 5/1988 | European Pat. Off. . |
| 0269876 | 6/1988 | European Pat. Off. . |
| 0271204 | 6/1988 | European Pat. Off. . |
| 0277723 | 8/1988 | European Pat. Off. . |
| 0279097 | 8/1988 | European Pat. Off. . |
| 0279574 | 8/1988 | European Pat. Off. . |
| 0281251 | 9/1988 | European Pat. Off. . |
| 0284232 | 9/1988 | European Pat. Off. . |
| 0286371 | 10/1988 | European Pat. Off. . |

(List continued on next page.)

Primary Examiner—Christopher L. Chin
Attorney, Agent, or Firm—William H. May; P. R. Harder; Merchant & Gould

[57] ABSTRACT

An assay device for the performance of assays for analytes, particularly those of biological interest, provides for improved efficiency and sensitivity by reducing background. The assay device performs an immunochromatographic assay and also provides a wash to remove unbound labeled specific binding partner and thereby reduce the background. Assay devices according to the present invention can use either a directly visible label such as a metal sol label or an enzyme label. One embodiment of assay devices according to the present invention is particularly suitable for assay of analytes in whole blood samples. The present invention also encompasses test kits and methods of use of the assay devices.

51 Claims, 15 Drawing Sheets

U.S. PATENT DOCUMENTS

| | | |
|---|---|---|
| 4,042,335 | 8/1977 | Clement . |
| 4,055,394 | 10/1977 | Friedman et al. . |
| 4,066,403 | 1/1978 | Bruschi . |
| 4,094,647 | 6/1978 | Deutsch et al. . |
| 4,108,729 | 8/1978 | Mennen . |
| 4,110,079 | 8/1978 | Schaeffer et al. . |
| 4,144,306 | 3/1979 | Figueras . |
| 4,153,668 | 5/1979 | Hill et al. . |
| 4,160,008 | 7/1979 | Fenocketti et al. . |
| 4,168,146 | 9/1979 | Grubb et al. . |
| 4,180,383 | 12/1979 | Johnson . |
| 4,189,304 | 2/1980 | Adams, Jr. et al. . |
| 4,200,690 | 4/1980 | Root et al. . |
| 4,212,742 | 7/1980 | Solomon et al. . |
| 4,225,557 | 9/1980 | Hartl et al. . |
| 4,233,029 | 11/1980 | Columbus . |
| 4,235,601 | 11/1980 | Deutsch et al. . |
| 4,246,339 | 1/1981 | Cole et al. . |
| 4,248,829 | 2/1981 | Kitajima et al. . |
| 4,248,965 | 2/1981 | Mochida et al. . |
| 4,254,083 | 3/1981 | Columbus . |
| 4,255,384 | 3/1981 | Kitajima et al. . |
| 4,256,693 | 3/1981 | Kondo et al. . |
| 4,258,001 | 3/1981 | Pierce et al. . |
| 4,271,119 | 6/1981 | Columbus . |
| 4,279,885 | 7/1981 | Reese et al. . |
| 4,288,228 | 9/1981 | Oberhardt . |
| 4,301,139 | 11/1981 | Feingers et al. . |
| 4,313,734 | 2/1982 | Leuvering . |
| 4,323,536 | 4/1982 | Columbus . |
| 4,337,065 | 6/1982 | Hiratsuka et al. . |
| 4,361,537 | 11/1982 | Deutsch et al. . |
| 4,363,874 | 12/1982 | Greenquist . |
| 4,365,970 | 12/1982 | Lawrence et al. . |
| 4,366,241 | 12/1982 | Tom et al. . |
| 4,376,110 | 3/1983 | David et al. . |
| 4,380,580 | 4/1983 | Boguslaski et al. . |
| 4,390,343 | 6/1983 | Walter . |
| 4,391,904 | 7/1983 | Litman et al. . |
| 4,407,943 | 10/1983 | Cole et al. . |
| 4,411,518 | 10/1983 | Meserol et al. . |
| 4,425,438 | 1/1984 | Bauman et al. . |
| 4,426,451 | 1/1984 | Columbus . |
| 4,427,769 | 1/1984 | Adlecreutz . |
| 4,435,504 | 3/1984 | Zuk et al. . |
| 4,442,204 | 4/1984 | Greenquist et al. . |
| 4,446,232 | 5/1984 | Liotta et al. . |
| 4,447,526 | 5/1984 | Rupchock et al. . |
| 4,447,546 | 5/1984 | Hirschfeld . |
| 4,459,358 | 7/1984 | Berke . |
| 4,472,498 | 9/1984 | Masuda et al. . |
| 4,474,878 | 10/1984 | Halbert et al. . |
| 4,477,575 | 10/1984 | Vogel et al. . |
| 4,486,530 | 12/1984 | David et al. . |
| 4,486,536 | 12/1984 | Baker et al. . |
| 4,515,889 | 5/1985 | Klose et al. . |
| 4,517,288 | 5/1985 | Giegel et al. . |
| 4,578,358 | 3/1986 | Oksman et al. . |
| 4,582,811 | 4/1986 | Pucci et al. . |
| 4,587,102 | 5/1986 | Nagatomo et al. . |
| 4,594,327 | 6/1986 | Zuk et al. . |
| 4,613,567 | 9/1986 | Yasoshima et al. . |
| 4,615,983 | 10/1986 | Koyama . |
| 4,623,461 | 11/1986 | Hossom et al. . |
| 4,624,929 | 11/1986 | Ullman . |
| 4,631,174 | 12/1986 | Kondo . |
| 4,632,901 | 12/1986 | Valkirs et al. . |
| 4,637,978 | 1/1987 | Dappen . |
| 4,642,285 | 2/1987 | Halbert et al. . |
| 4,645,743 | 2/1987 | Baker et al. . |
| 4,656,129 | 4/1987 | Wagner . |
| 4,666,866 | 5/1987 | Krauth . |
| 4,668,619 | 5/1987 | Greenquist et al. . |
| 4,670,381 | 6/1987 | Frickey et al. . |
| 4,676,950 | 6/1987 | Foster . |
| 4,678,757 | 7/1987 | Rapkin et al. . |
| 4,683,197 | 7/1987 | Gallati . |
| 4,690,907 | 9/1987 | Hibino et al. . |
| 4,693,834 | 9/1987 | Hossom . |
| 4,703,017 | 10/1987 | Campbell et al. . |
| 4,717,656 | 1/1988 | Swanljung . |
| 4,727,019 | 2/1988 | Valkirs et al. . |
| 4,738,823 | 4/1988 | Engelmann . |
| 4,740,468 | 4/1988 | Weng et al. . |
| 4,742,002 | 5/1988 | Guadagno . |
| 4,743,560 | 5/1988 | Campbell et al. . |
| 4,752,562 | 6/1988 | Sheiman et al. . |
| 4,753,776 | 6/1988 | Hillman et al. . |
| 4,756,828 | 7/1988 | Litman et al. . |
| 4,757,002 | 7/1988 | Joo . |
| 4,757,004 | 7/1988 | Houts et al. . |
| 4,761,381 | 8/1988 | Blatt et al. . |
| 4,770,853 | 9/1988 | Bernstein . |
| 4,775,636 | 10/1988 | Moeremans et al. . |
| 4,780,280 | 10/1988 | Berger et al. . |
| 4,786,594 | 11/1988 | Khanna et al. . |
| 4,789,526 | 12/1988 | Matkovich . |
| 4,789,628 | 12/1988 | Baker et al. . |
| 4,790,979 | 12/1988 | Terminiello et al. . |
| 4,797,260 | 1/1989 | Parker . |
| 4,804,518 | 2/1989 | Levine et al. . |
| 4,806,311 | 2/1989 | Greenquist . |
| 4,806,312 | 2/1989 | Greenquist . |
| 4,810,470 | 3/1989 | Burkhardt et al. . |
| 4,812,293 | 3/1989 | McLaurin et al. . |
| 4,816,224 | 3/1989 | Vogel et al. . |
| 4,818,677 | 4/1989 | Hay-Kaufman et al. . |
| 4,826,759 | 5/1989 | Guire et al. . |
| 4,837,145 | 6/1989 | Liotta . |
| 4,837,373 | 6/1989 | Gunkel et al. . |
| 4,839,297 | 6/1989 | Freitag et al. . |
| 4,847,199 | 7/1989 | Snyder et al. . |
| 4,851,356 | 7/1989 | Canfield et al. . |
| 4,853,335 | 8/1989 | Olsen et al. . |
| 4,855,240 | 8/1989 | Rosenstein et al. . |
| 4,857,453 | 8/1989 | Ullman et al. . |
| 4,859,612 | 8/1989 | Cole et al. . |
| 4,861,711 | 8/1989 | Friesen et al. . |
| 4,868,108 | 9/1989 | Bahar et al. . |
| 4,870,005 | 9/1989 | Akiyoshi et al. . |
| 4,876,067 | 10/1989 | Deneke et al. . |
| 4,877,586 | 10/1989 | Devaney, Jr. et al. . |
| 4,879,215 | 11/1989 | Weng et al. . |
| 4,883,764 | 11/1989 | Kloepfer . |
| 4,895,809 | 1/1990 | Schlabach et al. . |
| 4,900,663 | 2/1990 | Wie et al. . |
| 4,902,629 | 2/1990 | Meserol et al. . |
| 4,904,583 | 2/1990 | Mapes et al. . |
| 4,912,034 | 3/1990 | Kaira et al. . |
| 4,916,056 | 4/1990 | Brown, III et al . |
| 4,916,078 | 4/1990 | Klose et al. . |
| 4,918,025 | 4/1990 | Grenner . |
| 4,920,045 | 4/1990 | Okuda et al. . |
| 4,920,046 | 4/1990 | McFarland et al. . |
| 4,931,385 | 6/1990 | Block et al. . |
| 4,933,092 | 6/1990 | Aunet et al. . |
| 4,938,927 | 7/1990 | Kelton et al. . |
| 4,939,098 | 7/1990 | Suzuki et al. . |
| 4,943,522 | 7/1990 | Eisinger et al. . |
| 4,945,205 | 7/1990 | Litman et al. . |
| 4,952,517 | 8/1990 | Bahar . |
| 4,956,275 | 9/1990 | Zuk et al. . |

| | | |
|---|---|---|
| 4,956,302 | 9/1990 | Gordon et al. . |
| 4,959,305 | 9/1990 | Woodrum . |
| 4,959,307 | 9/1990 | Olson . |
| 4,959,324 | 9/1990 | Ramel et al. . |
| 4,960,691 | 10/1990 | Gordon et al. . |
| 4,963,325 | 10/1990 | Lennon et al. . |
| 4,963,468 | 10/1990 | Olson . |
| 4,965,047 | 10/1990 | Hammond . |
| 4,973,549 | 11/1990 | Khanna et al. . |
| 4,976,926 | 12/1990 | Matkovich . |
| 4,977,078 | 12/1990 | Niimura et al. . |
| 4,981,786 | 1/1991 | Dafforn et al. . |
| 4,988,627 | 1/1991 | Smith-Lewis . |
| 4,999,285 | 3/1991 | Stiso . |
| 4,999,287 | 3/1991 | Allen et al. . |
| 5,006,464 | 4/1991 | Chu et al. . |
| 5,006,474 | 4/1991 | Horstman et al. . |
| 5,009,996 | 4/1991 | Shah et al. . |
| 5,009,997 | 4/1991 | Shah et al. . |
| 5,013,669 | 5/1991 | Peters, Jr. et al. . |
| 5,028,535 | 7/1991 | Buechler et al. . |
| 5,030,555 | 7/1991 | Clemmons . |
| 5,030,558 | 7/1991 | Litman et al. . |
| 5,039,607 | 8/1991 | Skold et al. . |
| 5,051,237 | 9/1991 | Grenner . |
| 5,055,195 | 10/1991 | Trasch et al. . |
| 5,064,541 | 11/1991 | Jeng et al. . |
| 5,064,766 | 11/1991 | Wardlaw et al. . |
| 5,071,746 | 12/1991 | Wilk et al. . |
| 5,073,484 | 12/1991 | Swanson et al. . |
| 5,075,078 | 12/1991 | Osikowicz et al. . |
| 5,076,925 | 12/1991 | Roesink et al. . |
| 5,079,142 | 1/1992 | Coleman et al. . |
| 5,079,174 | 1/1992 | Buck et al. . |
| 5,085,987 | 2/1992 | Olson . |
| 5,085,988 | 2/1992 | Olson . |
| 5,087,556 | 2/1992 | Ertinghausen . |
| 5,089,391 | 2/1992 | Buechler et al. . |
| 5,094,956 | 3/1992 | Grow et al. . |
| 5,096,809 | 3/1992 | Chen et al. . |
| 5,096,837 | 3/1992 | Fan et al. . |
| 5,100,619 | 3/1992 | Baker et al. . |
| 5,104,793 | 4/1992 | Buck . |
| 5,104,811 | 4/1992 | Berger et al. . |
| 5,104,812 | 4/1992 | Kurn et al. . |
| 5,106,582 | 4/1992 | Baker . |
| 5,106,758 | 4/1992 | Adler et al. . |
| 5,110,550 | 5/1992 | Schlipfenbacher et al. . |
| 5,114,673 | 5/1992 | Berger et al. . |
| 5,118,428 | 6/1992 | Sand et al. . |
| 5,118,472 | 6/1992 | Tanaka et al. . |
| 5,120,504 | 6/1992 | Petro-Roy et al. . |
| 5,120,643 | 6/1992 | Ching et al. . |
| 5,120,662 | 6/1992 | Chan et al. . |
| 5,130,258 | 7/1992 | Makino et al. . |
| 5,132,208 | 7/1992 | Freitag et al. . |
| 5,135,719 | 8/1992 | Hillman et al. . |
| 5,135,873 | 8/1992 | Patel et al. . |
| 5,137,804 | 8/1992 | Greene et al. . |
| 5,137,808 | 8/1992 | Ullman et al. . |
| 5,141,850 | 8/1992 | Cole et al. . |
| 5,145,784 | 9/1992 | Cox et al. . |
| 5,156,952 | 10/1992 | Litman et al. . |
| 5,156,953 | 10/1992 | Litman et al. . |
| 5,158,869 | 10/1992 | Pouletty et al. . |
| 5,160,486 | 11/1992 | Schlipfenbacher et al. . |
| 5,162,238 | 11/1992 | Eikmeier et al. . |
| 5,164,294 | 11/1992 | Skold et al. . |
| 5,169,789 | 12/1992 | Bernstein . |
| 5,171,529 | 12/1992 | Schreiber . |
| 5,177,021 | 1/1993 | Kondo . |
| 5,182,191 | 1/1993 | Fan et al. . |
| 5,185,127 | 2/1993 | Vonk . |
| 5,188,939 | 2/1993 | Mangold et al. . |
| 5,188,966 | 2/1993 | Eikmeier et al. . |
| 5,200,317 | 4/1993 | Georgevich . |
| 5,200,321 | 4/1993 | Kidwell . |
| 5,202,268 | 4/1993 | Kuhn et al. . |
| 5,206,177 | 4/1993 | DeLaCroix . |
| 5,209,904 | 5/1993 | Forney et al. . |
| 5,212,060 | 5/1993 | Maddox . |
| 5,215,713 | 6/1993 | Steinbiss . |
| 5,223,436 | 6/1993 | Freitag et al. . |
| 5,232,663 | 8/1993 | Wilk et al. . |
| 5,232,835 | 8/1993 | Litman et al. . |
| 5,234,813 | 8/1993 | McGeehan et al. . |
| 5,238,652 | 8/1993 | Sun et al. . |
| 5,238,847 | 8/1993 | Steinbiss et al. . |
| 5,240,862 | 8/1993 | Koenhen et al. . |
| 5,252,293 | 10/1993 | Drbal et al. . |
| 5,256,372 | 10/1993 | Brooks et al. . |
| 5,258,163 | 11/1993 | Krause et al. . |
| 5,260,193 | 11/1993 | Olson . |
| 5,260,194 | 11/1993 | Olson . |
| 5,260,221 | 11/1993 | Ramel et al. . |
| 5,260,222 | 11/1993 | Patel et al. . |
| 5,262,067 | 11/1993 | Wilk et al. . |
| 5,264,180 | 11/1993 | Allen et al. . |
| 5,273,888 | 12/1993 | Guadagno . |
| 5,275,785 | 1/1994 | May et al. . |
| 5,306,623 | 4/1994 | Kiser et al. . |
| 5,308,580 | 5/1994 | Clark . |
| 5,308,775 | 5/1994 | Donovan et al. . |
| 5,314,804 | 5/1994 | Boguslaski et al. . |
| 5,338,513 | 8/1994 | Schlipfenbacher et al. . |
| 5,354,692 | 10/1994 | Yang et al. . |
| 5,364,533 | 11/1994 | Ogura et al. . |
| 5,395,754 | 3/1995 | Lambotte et al. . |
| 5,397,479 | 3/1995 | Kass et al. . |
| 5,401,667 | 3/1995 | Koike . |
| 5,416,000 | 5/1995 | Allen et al. . |
| 5,424,220 | 6/1995 | Goerlach-Graw et al. . |
| 5,435,970 | 7/1995 | Mamenta et al. . |
| 5,441,698 | 8/1995 | Norell . |
| 5,451,504 | 9/1995 | Fitzpatrick et al. . |
| 5,458,852 | 10/1995 | Buechler . |
| 5,468,647 | 11/1995 | Skold et al. . |
| 5,468,648 | 11/1995 | Chandler .................................. 422/58 |
| 5,491,096 | 2/1996 | Sportsman . |
| 5,500,375 | 3/1996 | Lee-Own et al. . |
| 5,504,013 | 4/1996 | Senior . |
| 5,521,102 | 5/1996 | Boehringer et al. . |
| 5,540,888 | 7/1996 | Bunce et al. . |
| 5,547,848 | 8/1996 | Shinoki et al. . |
| 5,559,041 | 9/1996 | Kang et al. . |
| 5,569,589 | 10/1996 | Hiraoka et al. . |
| 5,569,608 | 10/1996 | Sommer . |
| 5,573,921 | 11/1996 | Behnke et al. . |
| 5,591,645 | 1/1997 | Rosenstein . |
| 5,648,274 | 7/1997 | Chandler .................................. 436/514 |
| 5,656,503 | 8/1997 | May et al. . |

FOREIGN PATENT DOCUMENTS

| | | |
|---|---|---|
| 0291194 | 11/1988 | European Pat. Off. . |
| 0296724 | 12/1988 | European Pat. Off. . |
| 0297292 | 1/1989 | European Pat. Off. . |
| 0299359 | 1/1989 | European Pat. Off. . |
| 0299428 | 1/1989 | European Pat. Off. . |
| 0306772 | 3/1989 | European Pat. Off. . |
| 0317001 | 5/1989 | European Pat. Off. . |
| 0322340 | 6/1989 | European Pat. Off. . |
| 0323605 | 7/1989 | European Pat. Off. . |
| 0383619 | 8/1990 | European Pat. Off. . |
| 0415679 | 3/1991 | European Pat. Off. . |

| | | | | | |
|---|---|---|---|---|---|
| 0420021 | 4/1991 | European Pat. Off. . | WO 86/03839 | 7/1986 | WIPO . |
| 0443231 | 8/1991 | European Pat. Off. . | WO 86/04683 | 8/1986 | WIPO . |
| 0447154 | 9/1991 | European Pat. Off. . | WO 87/02774 | 5/1987 | WIPO . |
| 0516095 | 12/1992 | European Pat. Off. . | WO 87/02778 | 5/1987 | WIPO . |
| 0560410 | 9/1993 | European Pat. Off. . | WO 89/03992 | 5/1989 | WIPO . |
| 0560411 | 9/1993 | European Pat. Off. . | WO 89/06799 | 7/1989 | WIPO . |
| 2016687 | 9/1979 | United Kingdom . | WO 89/06801 | 7/1989 | WIPO . |
| 2173304 | 10/1986 | United Kingdom . | WO 91/01003 | 1/1991 | WIPO . |
| 2201241 | 8/1988 | United Kingdom . | WO 91/19980 | 12/1991 | WIPO . |
| 2204398 | 11/1988 | United Kingdom . | WO 92/01266 | 1/1992 | WIPO . |
| WO 82/02211 | 7/1982 | WIPO . | WO 93/03176 | 2/1993 | WIPO . |
| WO 84/02193 | 6/1984 | WIPO . | WO 95/13541 | 5/1995 | WIPO . |

OPPOSABLE-ELEMENT ASSAY DEVICE EMPLOYING UNIDIRECTIONAL FLOW

BACKGROUND OF THE INVENTION

This invention is directed to test strips for determination of characteristics of samples, unitized housings, kits incorporating the test strips, and methods of determining the characteristics of samples using the test strips.

Among the many analytical systems used for detection and/or determination of analytes, particularly analytes of biological interest, are chromatographic assay systems. Among the analytes frequently assayed with such systems are:

(1) hormones, such as human chorionic gonadotrophin (hCG), frequently assayed as a marker of human pregnancy;

(2) antigens, particularly antigens specific to bacterial, viral, and protozoan pathogens, such as Streptococcus, hepatitis virus, and Giardia;

(3) antibodies, particularly antibodies induced as a result of infection with pathogens, such as antibodies to the bacterium *Helicobacter pylori* and to human immunodeficiency virus (HIV);

(4) other proteins, such as hemoglobin, frequently assayed in determinations of fecal occult blood, an early indicator of gastrointestinal disorders such as colon cancer;

(5) enzymes, such as aspartate aminotransferase, lactate dehydrogenase, alkaline phosphatase, and glutamate dehydrogenase, frequently assayed as indicators of physiological function and tissue damage;

(6) drugs, both therapeutic drugs, such as antibiotics, tranquilizers, and anticonvulsants, and illegal drugs of abuse, such as cocaine, heroin, amphetamines, and marijuana; and (7) vitamins.

Such chromatographic systems are frequently used by physicians and medical technicians for rapid in-office diagnosis and therapeutic monitoring of a variety of conditions and disorders. They are also increasingly used by patients themselves for at-home monitoring of such conditions and disorders. Among the most important of such systems are the "thin layer" systems in which a solvent moves across a thin, flat absorbent medium.

Among the most important of tests that can be performed with such thin layer systems are immunoassays, which depend on the specific interaction between an antigen or hapten and a corresponding antibody or other specific binding partner. The use of immunoassays as a means of testing for the presence and/or amount of clinically important molecules has been known for some time. As early as 1956, J. M. Singer reported the use of an immune-based latex agglutination test for detecting a factor associated with rheumatoid arthritis (Singer et al., *Am. J. Med.* 22:888–892 (1956)).

Among the chromatographic techniques used in conjunction with immunoassays is a procedure known as immunochromatography. In general, this technique uses a disclosing reagent or particle that has been linked to an antibody to the molecule to be assayed, forming a conjugate. This conjugate is then mixed with a specimen, and, if the molecule to be assayed is present in the specimen, the disclosing reagent-linked antibodies bind to the molecule to be assayed, thereby giving an indication that the molecule to be assayed is present. The disclosing reagent or particle can be identifiable by color, magnetic properties, radioactivity, specific activity with another molecule, or another physical or chemical property. The specific reactions that are employed vary with the nature of the molecule being assayed and the sample to be tested.

Immunochromatographic assays fall into two principal categories: "sandwich" and "competitive," according to the nature of the antigen-antibody complex to be detected and the sequence of reactions required to produce that complex. In general, the sandwich immunochromatographic procedures call for mixing the sample that may contain the analyte to be assayed with antibodies to the analyte. These antibodies are mobile and typically are linked to a label or disclosing reagent, such as dyed latex, a colloidal metal sol, or a radioisotope. This mixture is then applied to a chromatographic medium containing a band or zone. This band or zone contains immobilized antibodies to the analyte of interest. The chromatographic medium is often in the form of a strip resembling a dipstick. When the complex of the molecule to be assayed and labeled antibody reaches the zone of the immobilized antibodies on the chromatographic medium, binding occurs and the bound labeled antibodies are localized at the zone. This indicates the presence of the molecule to be assayed. This technique can be used to obtain quantitative or semi-quantitative results.

Examples of sandwich immunoassays performed on test strips are described by U.S. Pat. No. 4,168,146 to Grubb et al. and U.S. Pat. No. 4,366,241 to Tom et al., both of which are incorporated herein by this reference.

In addition to immunochromatographic assays, it is also known to use enzyme-based chromatographic assays. These techniques are roughly analogous to immunochromatographic assays, but use an enzymatically catalyzed reaction instead of an antigen-antibody reaction. The enzymatically catalyzed reaction frequently generates a detectable product. Other analogous chromatographic assays are known.

Although useful, currently available chromatographic techniques using test strips have a number of drawbacks. Many samples, such as fecal samples, contain particulate matter that can clog the pores of the chromatographic medium, greatly hindering the immunochromatographic process. Other samples, such as blood, contain cells and colored components that make it difficult to read the test. Even if the sample does not create interference, it is frequently difficult with existing chromatographic test devices to apply the sample to the chromatographic medium so that the sample front moves uniformly through the chromatographic medium to ensure that the sample reaches the area where binding is to occur in a uniform, straight-line manner.

Sample preparation and waste generation are responsible for other problems with currently available devices and techniques for immunochromatography. The increased prevalence of diseases spread by infected blood and blood fractions, such as AIDS and hepatitis, has exacerbated these problems. It is rarely possible to apply a sample (such as feces) or a sampling device (such as a throat swab) directly to the chromatographic medium. Several extraction and pretreatment reactions are usually required before the sample can be applied to the chromatographic medium. These reactions are typically carried out by the physician or technician performing the test in several small vessels, such as test tubes or microfuge tubes, requiring the use of transfer devices such as pipettes. Each of these devices is then contaminated and must be disposed of using special precautions so that workers or people who may inadvertently come into contact with the waste do not become contaminated.

When blood samples are involved, there are additional considerations. Whole blood samples are most easily accommodated by a reverse flow format, i.e., one that performs bidirectional chromatography. The reverse flow format has the advantage of allowing the test results to be read against the cleared, white chromatographic medium, eliminating the potential for obscuring weak test results. However, in such a reverse flow format, the amount of sample that is brought into contact with the capture line is very limited. In a typical assay, approximately 3–5 μl of the applied sample is utilized, and hence assay sensitivity is "capture limited." This is especially true if the immunological reagents used are of low affinity or avidity for the performance of immunochromatographic assays or other analogous assays. Therefore, it would be desirable to have an immunochromatographic assay device that could perform assays for analytes found in blood with a undirectional assay format.

Additionally, such a device should be capable of receiving a possibly contaminated sample or a sample preparation device directly so as to eliminate the need for extraction vessels and transfer devices. Such a device, preferably in the form of a test strip, should also be capable of performing immunochromatographic assays on colored samples or samples containing particulates without interference and should be able to deliver the sample to the chromatographic medium uniformly and evenly to improve accuracy and precision of the test. This aspect of an improved assay device is particularly important in avoiding false negatives and false positives. In particular, an improved assay device should also be capable of performing a unidirectional assay on a whole blood sample.

SUMMARY

I have developed an assay device that meets these needs and provides improved assays for analytes of biological interest, particularly using whole blood samples, while simplifying the performance of the assay and avoiding contamination. The device can perform all types of immunoassays, including sandwich immunoassays, competitive immunoassays, and assays employing combinations of these principles, but is particularly adapted to the performance of sandwich immunoassays.

One embodiment of the present invention is a chromatographic assay device for detection and/or determination of an analyte comprising:

(1) a first opposable component including:
  (a) a sample preparation zone for receiving a sample to be assayed; and
  (b) a chromatographic medium having first and second ends and having a detection zone containing an immobilized specific binding partner for the analyte, the chromatographic medium being separated from the sample preparation zone on the first opposable component; and
(2) a second opposable component including:
  (a) a conductor;
  (b) an absorber separated from the conductor; and
  (c) an applicator separated on the second opposable component from the conductor and the absorber.

In this device, the first and second opposable components are configured so that bringing the first and second opposable components into operable contact results in the absorber coming into operable contact with the second end of the chromatographic medium, the conductor coming into operable contact with the sample preparation zone and the first end of the chromatographic medium, and results in the applicator coming into operable contact with the sample preparation zone so that the sample preparation zone bridges the applicator and the conductor, and so that the chromatographic medium bridges the conductor and the absorber.

Typically, the sample preparation zone includes a labeled specific binding partner for the analyte in resolubilizable form. Typically, the sample preparation zone contains at least one reagent for treatment of the sample before the sample is applied to the chromatographic medium. Preferably, the reagent for treatment of the sample is an extraction reagent to extract analyte from the sample.

Preferably, the label of the labeled specific binding partner is a visible label.

The chromatographic medium can further includes a control zone separate from the detection zone. Typically, the control zone contains analyte immobilized thereto.

Typically, at least one of the first and second opposable components includes an aperture therein for viewing of at least a portion of the chromatographic medium.

These optional features can also be present in other embodiments of assay devices according to the present invention, as described below.

Another embodiment of the present invention is an assay device with multiple sample preparation zones. This embodiment comprises:

(1) a first opposable component including:
  (a) a plurality of labeled specific binding partner applicators, each labeled specific binding partner applicator for applying a labeled specific binding partner for the analyte to the chromatographic medium; and
  (b) a chromatographic medium having first and second ends and including a detection zone containing an immobilized specific binding partner for the analyte, the chromatographic medium being separated from the labeled specific binding partner applicators on the first opposable component, the labeled specific binding partner applicator located furthest from the chromatographic medium for receiving a sample to be assayed; and
(2) a second opposable component including;
  (a) at least one conductor, with there being at least as many conductors as the number of labeled specific binding partner applicators on the first opposable component minus one, the conductors being located on the second opposable component such that, when the first and second opposable component are brought into operable contact, one conductor is in operable contact with a labeled specific binding partner applicator and the chromatographic medium and the other conductors are in operable contact with two labeled specific binding partner applicators;
  (b) an absorber separated from the conductors on the second opposable components; and
  (iii) a wash liquid applicator separated on the second opposable component from the conductors and absorber.

In this embodiment of the assay device, bringing the first and second opposable components into operable contact causes the absorber to come into operable contact with the second end of the chromatographic medium, causes the conductors to come into operable contact with the sample preparation zones, and causes the wash liquid applicator to come into operable contact with the labeled specific binding partner applicator that is located the farthest from the chromatographic medium.

Yet another embodiment of the present invention is particularly suitable for use with a specific binding partner labeled with a catalyst, such as an enzyme. This embodiment comprises:

(1) a first opposable component including
(a) a chromatographic medium having first and second ends and including a detection zone containing an immobilized specific binding partner for the analyte;
(b) a sample preparation zone for receiving a sample to be assayed, the sample preparation zone including a catalyst-labeled specific binding partner for the analyte in resolubilizable form, the sample preparation zone being separated from the chromatographic medium; and
(c) a first applicator containing a substance that participates in a reaction catalyzed by the catalyst to produce a detectable product, the first applicator being separated on the first opposable component from the chromatographic medium and the sample preparation zone; and
(2) a second opposable component including:
(a) a second applicator;
(b) a conductor; and
(c) an absorber separated from the conductor and the second applicator.

In this embodiment, the first and second opposable components are configured such that bringing the first and second opposable components into operable contact causes the second applicator to come into operable contact with both the first applicator and the sample preparation zone, causes the conductor to come into operable contact with both the sample preparation zone and the first end of the chromatographic medium, and causes the absorber to come into operable contact with the second end of the chromatographic medium.

Typically, the catalyst is an enzyme. Typically, the enzyme is selected from the group consisting of horseradish peroxidase, alkaline phosphatase, β-galactosidase, and glucose oxidase.

In one preferred alternative, the substance that participates in a reaction is a substrate that is converted to an insoluble product that is deposited at the detection zone as the result of the action of the catalyst.

Another embodiment of the present invention is particularly suitable for assay of whole blood samples. This embodiment comprises:
(1) a first opposable component including;
(a) a sample preparation zone containing a matrix of porous material permeable to the liquid portion of blood but capable of trapping the cellular components of blood;
(b) a first applicator containing a labeled specific binding partner for the analyte in resolubilizable form in operable contact with the sample preparation zone; and
(c) a chromatographic medium including a detection zone containing an immobilized specific binding partner for the analyte, the chromatographic medium being in operable contact with the first applicator, the chromatographic medium, first applicator, and sample preparation zone being so located that the first applicator is between the sample preparation zone and the chromatographic medium; and
(2) a second opposable component including:
(a) a second applicator; and
(b) an absorber.

In this embodiment, the first and second opposable components are configured so that bringing the first and second opposable components into operable contact causes the second applicator to come into operable contact with the first applicator to apply a wash liquid thereto and causes the absorber to come into operable contact with the second end of the chromatographic medium. Preferably, a barrier, such as a clear, self-adhesive film, prevents the second applicator from coming into operable contact with the sample preparation zone and thus prevents liquid flow between the second applicator and the sample preparation zone.

In one alternative, the matrix can contain a binder for the cellular components of blood. The binder can be an anti-blood cell antibody, preferably an anti-erythrocyte antibody. Alternatively, the binder can be a lectin.

As another alternative, the matrix can be impregnated with a carbohydrate capable of aggregating blood cells; preferably, the carbohydrate is mannitol.

As yet another alternative, the sample preparation zone can include an asymmetric membrane.

Another embodiment of the present invention is multiplex devices that can perform more than one assay simultaneously on the same device. These multiplex devices are based on the embodiments described above.

One alternative version of a multiplex device comprises:
(1) a first opposable component including:
(a) a plurality of laterally separated sample preparation zones, each sample preparation zone for receiving a sample to be assayed; and
(b) a plurality of laterally separated chromatographic media, each chromatographic medium having first and second ends and including therein a detection zone containing an immobilized specific binding partner for an analyte, each chromatographic medium being located in a line with a sample preparation zone; and
(2) a second opposable component including:
(a) a plurality of laterally separated conductors;
(b) a plurality of laterally separated absorbers, each absorber being located in line with a conductor; and
(c) a plurality of laterally separated applicators, each applicator being located in line with an absorber and a conductor.

In this embodiment, when the first and second opposable components are brought into operable contact, each applicator is brought into operable contact with a corresponding sample preparation zone, each conductor is brought into operable contact with a corresponding sample preparation zone and with a corresponding chromatographic medium, and each absorber is brought into operable contact with the second end of a corresponding chromatographic medium.

Another alternative version of a multiplex device comprises:
(1) a first opposable component including:
(a) a plurality of laterally separated chromatographic media, each chromatographic medium having first and second ends and including thereon a detection zone containing an immobilized specific binding partner for an analyte;
(b) for each chromatographic medium, a plurality of labeled specific binding partner applicators for applying a labeled specific binding partner for an analyte to the chromatographic medium, the labeled specific binding partner applicator located furthest from the chromatographic medium for receiving a sample to be assayed, each chromatographic medium being located on the first opposable component in line with an equal number of labeled specific binding partner applicators; and
(2) a second opposable component including:
(a) a plurality of laterally-separated wash liquid applicators, one applicator for each chromatographic medium;

(b) a plurality of laterally-separated conductors, each conductor being located in line with a wash liquid applicator, with there being at least as many conductors for each chromatographic medium as the number of labeled specific binding partner applicators minus one for each chromatographic medium; and (c) a plurality of laterally-separated absorbers, one absorber for each chromatographic medium, each absorber being located in line with a wash liquid applicator and a conductor.

In this embodiment, when the first and second opposable components are brought into opposition, each wash liquid applicator is brought into operable contact with a corresponding labeled specific binding partner applicator, the corresponding labeled specific binding partner applicators being those that are located the farthest from each chromatographic medium, each conductor is brought into operable contact with either two corresponding labeled specific binding partner applicators or a corresponding labeled specific binding partner applicator and the first end of a corresponding chromatographic medium, and each absorber is brought into operable contact with the second end of a corresponding chromatographic medium.

Another alternative version of a multiplex device comprises:

(1) a first opposable component including:

(a) a plurality of laterally-separated chromatographic media, each chromatographic medium having first and second ends and including thereon a detection zone containing an immobilized specific binding partner for an analyte;

(b) a plurality of laterally-separated sample preparation zones, one for each chromatographic medium, each sample preparation zone including a specific binding partner for an analyte in a resolubilizable form labeled with a catalyst, each sample preparation zone being in line with a chromatographic medium; and (c) a plurality of first applicators, one for each chromatographic medium, each first applicator containing a substrate that participates in a reaction catalyzed by the catalyst, the reaction forming a detectable product, each first applicator being in line with a chromatographic medium and a sample preparation zone; and (2) a second opposable component including:

(a) a plurality of laterally-separated second applicators, one second applicator for each chromatographic medium;

(b) a plurality of laterally-separated conductors, one conductor for each chromatographic medium, each conductor being in line with a second applicator; and (c) a plurality of laterally-separated absorbers, one absorber for each chromatographic medium, each absorber being in line with a second applicator and a conductor.

In this embodiment, the first and second opposable components are configured so that bringing the first and second opposable components into operable contact causes each second applicator to come into operable contact with a corresponding first applicator and sample preparation zone, causes each conductor to come into operable contact with a corresponding sample preparation zone and chromatographic medium via the first end of the chromatographic medium, and causes each absorber to come into operable contact with a corresponding chromatographic medium via the second end of each chromatographic medium.

Yet another alternative version of a multiplex device comprises:

(1) a first opposable component including:

(a) a plurality of laterally-separated chromatographic media, each chromatographic medium having first and second ends and including thereon a detection zone containing an immobilized specific binding partner for an analyte;

(b) a plurality of laterally-separated first applicators, one first applicator for each chromatographic medium, each first applicator being in operable contact with the first end of a corresponding chromatographic medium; and (c) a plurality of laterally-separated sample preparation zones, each sample preparation zone being in operable contact with a corresponding first applicator, each sample preparation zone including therein a matrix of porous material permeable to the liquid portion of blood but capable of trapping the cellular components of blood; and (2) a second opposable component including:

(a) a plurality of laterally-separated second applicators, one for each chromatographic medium; and (b) a plurality of laterally-separated absorbers, one for each chromatographic medium, each absorber being in line with a second applicator.

In this embodiment, the first and second opposable components are configured so that bringing the first and second opposable components into operable contact causes each second applicator to come into operable contact with the corresponding sample preparation zone and first applicator and causes each absorber to come into operable contact with the corresponding chromatographic medium via the second end of the chromatographic medium.

Another aspect of the present invention is test kits for detection and/or determination of analytes. These test kits include, separately packaged:

(1) an assay device according to the present invention;

(2) a wash liquid to be applied to the appropriate applicator on the second opposable component; and, optionally, (3) any additional reagents for treating or extracting the sample.

Yet another aspect of the present invention is methods of use of assay devices according to the present invention. In general, these methods involve applying a sample to the sample preparation zone of the device, applying a wash liquid to an applicator of the device, allowing the sample to migrate through the chromatographic medium, closing the device to apply the wash liquid, and detecting and/or determining the analyte by observing and/or measuring the labeled specific binding partner bound at the detection zone.

BRIEF DESCRIPTION OF THE DRAWINGS

These and other features, aspects, and advantages of the present invention will become better understood with reference to the following description, appended claims, and accompanying drawings where:

DESCRIPTION

Definitions

Figure 1:
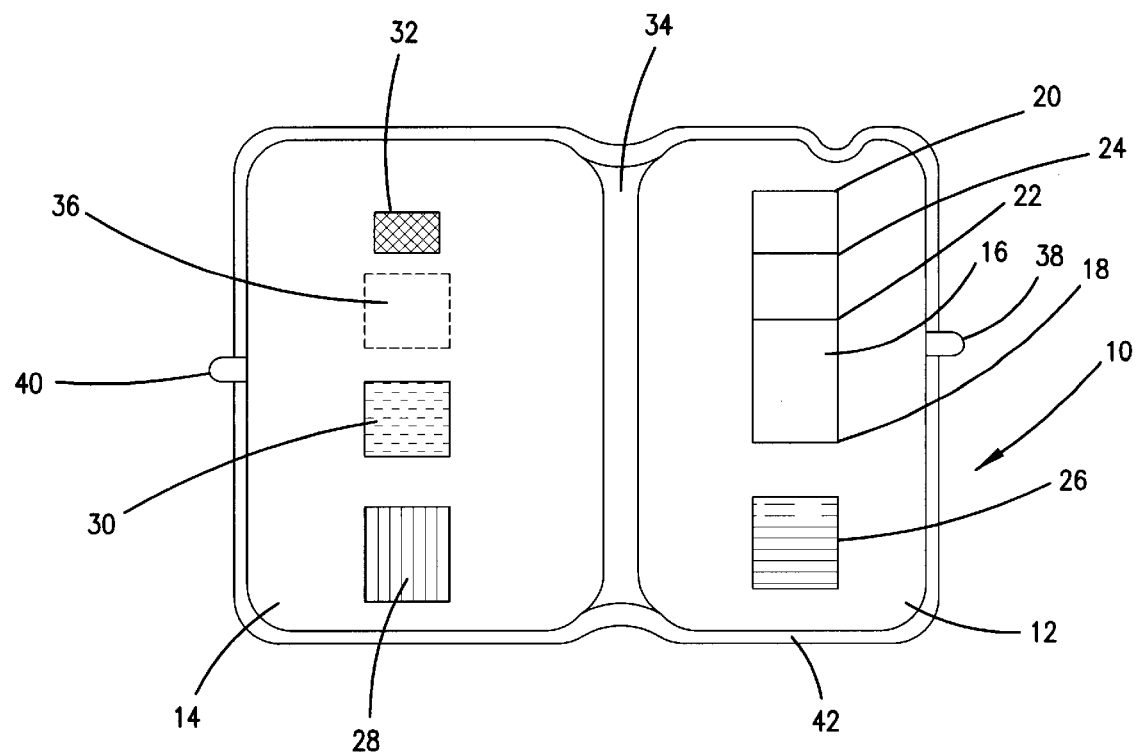
FIG. 1 is a drawing of a first embodiment of an assay device according to the present invention.

In the context of this disclosure, the following terms are defined as follows unless otherwise indicated:

Specific Binding Partner: A member of a pair of molecules that interact by means of specific noncovalent interactions that depend on the three-dimensional structures of the molecules involved. Typical pairs of specific binding partners include antigen-antibody, hapten-antibody, hormone-receptor, nucleic acid strand-complementary nucleic acid strand, substrate-enzyme, inhibitor-enzyme, carbohydrate-lectin, biotin-avidin, and virus-cellular receptor.

Operable Contact: Two solid components are in operable contact when they are in contact, either directly or indirectly, in such a manner that a liquid can flow from one of the two components to the other substantially uninterruptedly, by capillarity or otherwise. "Direct contact" means that the two elements are in physical contact, such as edge-to-edge or front-to-back. "Indirect contact" means that the two elements are not in physical contact, but are bridged by one or more conducting means. This bridging by one or more conducting means can be either edge-to-edge or front-to-back, such as by the opposition or bringing into contact of planar elements.

Analyte: The term "analyte" includes both the actual molecule to be assayed and analogues and derivatives thereof when such analogues and derivatives bind another molecule used in the assay in a manner substantially equivalent to that of the analyte itself.

Antibody: The term "antibody" includes both intact antibody molecules of the appropriate specificity, and antibody fragments (including Fab, F(ab), F(ab'), F(ab')$_2$, and Fv fragments), as well as chemically modified intact molecules and antibody fragments, including hybrid molecules assembled by in vitro reassociation of subunits. Also included are genetically engineered antibodies of the appropriate specificity, including single chain derivatives. Both polyclonal and monoclonal antibodies are included unless otherwise specified.

Secondary Specific Binding Partner: The term "secondary specific binding partner" is used to designate an additional specific binding partner that binds to a member of a pair of specific binding partners when the pair of specific binding partners is interacting. For example, a pair of specific binding partners can comprise Giardia antigen and rabbit anti-Giardia antibody. In that case, the secondary specific binding partner can be goat anti-rabbit Ig antibody. The secondary specific binding partner can be specific to the species, class, or subclass of an antibody specific binding partner to which it binds. Alternatively, when one of the specific binding partners is labeled with biotin, the secondary specific binding partner can comprise a molecule conjugated to avidin.

I. CHROMATOGRAPHIC ASSAY DEVICES

One aspect of the present invention comprises chromatographic assay devices particularly useful for the assay of analytes in biological samples. These devices are suitable for the direct application of biological samples, without preliminary extraction steps, and are constructed so as to minimize interference with assay results caused by particulates or colored samples.

These devices are intended to provide more homogenous mixing of the analyte and a labeled specific binding partner that is typically in resolubilizable form. In particular, one embodiment of devices according to the present invention is particularly adapted to the assay of analytes present in a whole blood sample.

The device has at least two substantially planar opposable components. One of these substantially planar components has on its surface a chromatographic medium.

When there are two opposable components, one of the opposable components has designated the first opposable component and the other is designated the second opposable component. This distinction is arbitrary and for convenience in description; the role of each of the opposable components is determined by the element or elements located on it.

The device also has means for opposing the opposable components, also referred to as bringing them into operable contact, and applying pressure thereto. The opposable components can be brought into opposition from a position which they are not in opposition by direct manual closure, i.e., by manipulation by the operator. The pressure applied is sufficient to transfer fluid from one opposable component to another opposable component in a direction substantially normal to the opposable components in a sequence determined by the construction of the assay device. The end result is that sample is applied to the chromatographic medium for detection and/or determination of the analyte thereon. The pressure also drives fluid through the chromatographic medium to accelerate the process of chromatography, giving a detectable result in less time. Additionally, the pressure makes possible the performance of steps, such as extraction steps, in the device, and can be used to remove excess fluid from the chromatographic medium by absorbers to reduce the background of the assays. The pressure is generated by placing the opposable components into opposition and maintained by holding the components in opposition by engagers such as locks or clasps, or, alternatively, by an adhesive strip along the outside margin of one of the components that allows sealing the components.

Devices according to the present invention can be constructed for the performance of either a sandwich or a competitive assay, but devices according to the present invention are particularly useful for sandwich immunoassays. As used herein, the term "immunoassay" is used generally to include specific binding assays need not necessarily be restricted to assays in which the specific binding partner is an antibody, unless so specified.

The degree of pressure employed in the device can be regulated so that it is optimum for the characteristics of the chromatographic medium, analyte, and label.

A. Elements Common to Devices According to the Present Invention

A number of elements are common to assay devices according to the present invention and are discussed here for convenience.

1. The Chromatographic Medium

The chromatographic medium is a strip. Typically, the strip is substantially planar, although this is not required in all applications. It is typically rectangular, having first and second ends and first and second surfaces. Throughout this description, the term "first end" refers to the end at or near which liquid is applied to the chromatographic medium and the term "second end" applies to the opposite end of the chromatographic medium. Liquid applied at or near the first end of the chromatographic medium can be, but is not necessarily, a sample or a treated sample, and can contain a resolubilized labeled specific binding partner for the analyte.

The chromatographic medium is composed of material suitable as a medium for thin layer chromatography of analyte and analyte-antibody conjugates, such as nitrocellulose, nylon, rayon, cellulose, paper, or silica. The chromatographic medium can be pretreated or modified as needed.

Typically, the chromatographic medium is translucent, so that colored zones appearing on it can be viewed from either side.

2. Absorbers

In a number of devices according to the present invention, absorbers are in operable contact with at least one end of the chromatographic medium. The absorbers can be made of any bibulous material that will hold a liquid sufficiently so that liquid can be drawn through the chromatographic medium and accumulated in the absorber. Typical materials include, but are not limited to, filter paper.

3. Other Fluid-Carrying Elements

As described below, in particular devices according to the present invention, other fluid-carrying elements can be employed as sample preparation zones, applicators, and/or conductors. These elements are prepared of hydrophilic media that pass liquids without substantially absorbing them. Such materials are well known in the art. In some cases, these elements can have incorporated therein a component in dry form that can be resolubilized by addition of a liquid to the element. Such components can include a labeled specific binding partner for the analyte or a substrate, coenzyme, or cofactor for the enzyme of an enzyme-labeled specific binding partner. The terms "resolubilized," "resolubilizable," and similar terminology are used herein generally to refer to the state of such components.

4. Opposable Components

Many of the embodiments of the assay device according to the present invention comprise two opposable components. The bodies of the opposable components are preferably made of laminated cardboard that is sufficiently impervious to moisture to contain the liquids involved in the performance of the assay carried out by the device. Other cellulose-based materials, such as paperboard or solid bleached sulfite (SBS) can also be used. Alternatively, the bodies of the opposable components can be made of plastic that is impervious to moisture. A suitable plastic is a polycarbonate plastic such as Lexan™.

The opposable components are joined by a hinge, preferably made of a material impermeable to liquids, such as a plastic that can be compatibly joined with or is the same as the material used for the first and second opposable components.

5. Labeled Components

For assay devices intended to perform a sandwich immunoassay, the labeled component is typically a labeled specific binding partner to the analyte. This labeled component is typically mobile, in that it can migrate through the chromatographic medium, whether free or bound to analyte. The label is preferably a visually detectable label, such as a colloidal metal label. Preferably, the colloidal metal label is gold, silver, bronze, iron, or tin; most preferably, it is gold. The preparation of gold labeled antibodies and antigens is described in J. DeMey, "The Preparation and Use of Gold Probes," in *Immunocytochemistry: Modern Methods and Applications* (J. M. Polak and S. Van Noorden, eds., Wright, Bristol, England, 1986), ch. 8, pp. 115–145, incorporated herein by this reference. Antibodies labeled with colloidal gold are commercially available, such as from Sigma Chemical Company, St. Louis, Mo. Alternatively, other colloidal labels, such as a colloidal sulfur label or a dye-silica label, can also be used. In a less preferred alternative, the visually detectable label can be a colored latex label. It is also possible to use other labels, such as a radioactive label, a fluorescent label, or an enzyme label.

In one particular embodiment of the invention, an enzyme label is preferred; the use of such enzyme labels is discussed below with respect to that embodiment.

C. Details of Devices According to the Present Invention

1. Bridged Device with Single Sample Preparation Zone

One embodiment of the present invention is a bridged device with a single sample preparation zone.

This device is shown in FIG. 1. The device 10 has a first opposable component 12 and a second opposable component 14. The first opposable component 12 has a chromatographic medium 16 with a first end 18 and a second end 20. The chromatographic medium 16 further includes a detection zone 22 and, optionally, a control zone 24. The detection zone 22 typically includes an immobilized specific binding partner for the analyte. The control zone 24 can, for example, comprise analyte immobilized to the chromatographic medium 16 so that a labeled specific binding partner can be bound at the control zone 24 to verify that the assay has been performed properly.

The first opposable component 12 further includes a sample preparation zone 26 for receiving a liquid sample. As used herein, the term "liquid sample" can include semisolid samples or samples containing particulate matter.

The reagents that can be present in the sample preparation zone 26 vary with the sample to be applied to the sample preparation zone 26 and with the analyte to be assayed. They can include, but are not limited to, acids or alkalis to adjust the pH, buffers to stabilize the pH, chelating agents such as EDTA or EGTA to chelate metals, surfactants to act as wetting agents, hydrolytic enzymes to lyse the cell membrane of animal cells or the cell wall of bacteria to liberate analytes, substrates or coenzymes for enzymes, and the like. One particularly useful extraction reagent is a mixture of sodium nitrite and acetic acid to generate nitrous acid. The sodium nitrite can be present in dried form on the sample preparation zone 26, and the acetic acid can be added to the sample preparation zone 26 after the addition of the sample.

The sample, or, optionally, a sampling device such as a throat swab or a microporous filter, can be placed by the operator on the sample preparation zone 26; if needed, other reagents can be added.

The second opposable component 14 includes an applicator 28 that is typically used for the addition of a wash liquid during the performance of the assay. The second opposable component 14 further includes a conductor 30 and an absorber 32. When the first and second opposable components 12 and 14 are brought into operable contact by closing the device 10, the applicator 28 is brought into operable contact with the sample preparation zone 26, and the conductor 30 is brought into operable contact with both the sample preparation zone 26 and the chromatographic medium 16 through its first end 18. The absorber 32 is also brought into operable contact with the chromatographic medium 16 through its second end 20.

In the operation of the device 10, a sample is applied to the sample preparation zone 26, and a wash liquid is applied to the applicator 28. The sample is then allowed to resolubilize the labeled specific binding partner in the sample preparation zone 26, if present. If the sample preparation zone 26 does not contain a labeled specific binding partner in resolubilizable form, a labeled specific binding partner can be added along with the sample. Alternatively, the conductor 30 could include a labeled specific binding partner in resolubilizable form, or both the sample preparation zone 26 and the conductor 30 could include the resolubilizable labeled specific binding partner. The first and second opposable components 12 and 14 are then brought into operable contact, allowing the sample and the resolubilized labeled specific binding partner to pass through the conductor 30 and then into and through the chromatographic medium 16. This fluid flow is driven by absorption of fluid by the absorber 28 which is now in operable contact with the second end 20 of the chromatographic medium 16. Subsequent to the flow of the sample and labeled specific binding partner through the chromatographic medium 16, the wash liquid applied to the applicator 28 passes through the sample preparation zone 26, the conductor 30, and the chromatographic medium 16, eventually reaching the absorber 32. This device can give a qualitative and/or quantitative indication of the analyte, depending upon the concentration of the labeled specific binding partner into detection zone and the size of the detection zone. As used herein, the term "detect" refers to a qualitative indication and the term "determine" refers to a quantitative or semiquantitative indication. Similarly, the term "observe" refers to a qualitative indication of the labeled specific binding partner bound at the detection zone and the term "measure" refers to a quantitative or semiquantitative indication.

The first and second opposable components 12 and 14 are joined by a hinge 34. At least one of the first and second opposable components 12 and 14 has an aperture 36 to allow for viewing of the chromatographic medium 16, including the detection zone 22, and where present, the control zone 24. In the version of the device 10 shown in FIG. 1, the aperture 36 is located in the second opposable component 14.

The first and second opposable components 12 and 14 preferably further comprise engagers that secure the first and second opposable components 12 and 14 in opposition or operable contact. The engagers can comprise locks, such as locks 38 and 40 that are engaged when the first opposable component 12 and the second opposable component 14 are brought into opposition. The construction and dimensions of the locks 38 and 40 can be varied to exert the optimal degree of pressure on the opposable components 12 and 14. The degree of pressure that is optimal may depend on the thickness and construction of the chromatographic medium 16, the intended sample volume, and other factors. Alternatively, the first and second opposable components 12 and 14 can be held in position by means of an adhesive strip that is applied to one of the first and second opposable components 12 and 14; the adhesive strip can be provided with a release liner. To guard against leakage of samples or reagents, a sealing ridge or gasket 42 can be positioned around the perimeter of the first and second opposable components 12 and 14. Although the use of the engagers, such as locks 38 and 40, or, alternatively, the adhesive strip, and the use of the sealing ridge or gasket 42, is generally preferred, these components are not necessary to construct a basic device according to the present invention.

The wash liquid, also referred to as running buffer, is typically an aqueous liquid; it can be water, or can contain buffers or electrolytes. It can be, for example, sodium phosphate, phosphate buffered saline, physiological saline, or another aqueous liquid. An example of a suitable wash liquid or running buffer is phosphate buffered saline.

Figure 2:
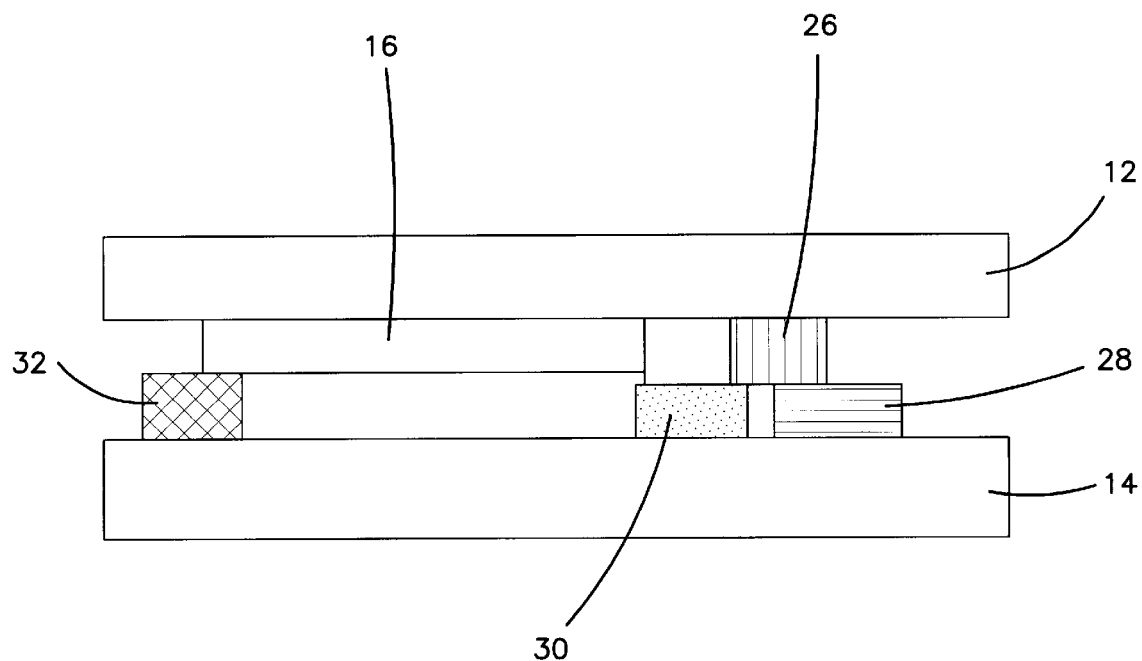
FIG. 2 is a schematic diagram showing the flow path of liquid through the device of FIG. 1.

In this embodiment of the device according to the present invention, the fluid flow path alternates between the first opposable component 12 and the second opposable component 14. The flow path is shown in FIG. 2.

Typically, to achieve results, the assay requires from 30 seconds to 10 minutes, more typically from 1 to 5 minutes, including any period of incubation of the sample on the sample preparation zone, as well as the time required for chromatography itself. Typically, the assay is performed at room temperature, although it can be performed at 4° C. or up to 37° C. or higher in some cases, depending on the nature of the analyte and the specific binding partners. In some cases, performing the assay at a lower temperature may be desirable to limit degradation, while in other cases, performing the assay at a higher temperature with suitable analytes and specific binding partners may speed up the assay.

In devices according to the present invention, a chromatographic assay is performed as a result of migration of the sample within the chromatographic medium. The analyte is detected at a position different than the position at which the sample is applied to the chromatographic medium.

2. Bridged Device with Multiple Labeled Specific Binding Partner Applicators

Along these principles, another embodiment of assay devices according to the present invention uses multiple labeled specific binding partner applicators that are bridged by multiple conductors. At least one of the labeled specific binding partner applicators also serves as a sample preparation zone. Typically, this is the labeled specific binding partner applicator located furthest from the chromatographic medium on the first opposable component.

Figure 3:
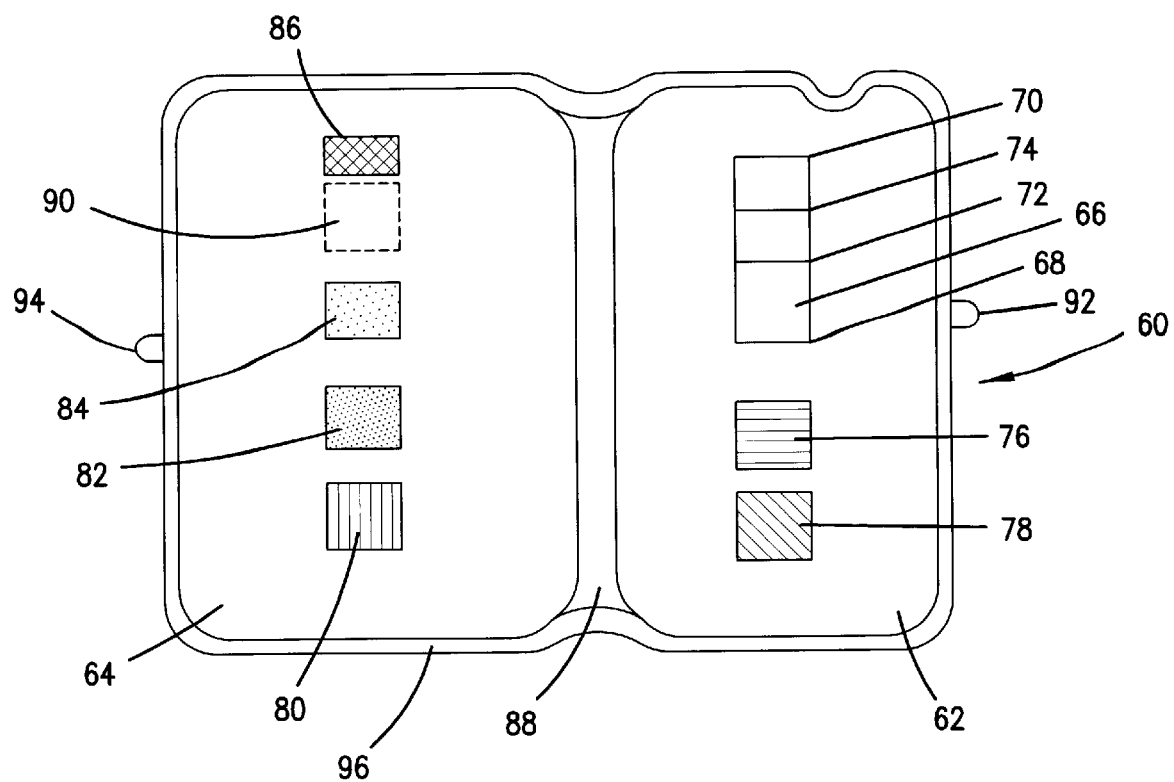
FIG. 3 is a drawing of a second embodiment of an assay device according to the present invention with multiple sample preparation zones.

This device is shown in FIG. 3. The device 60 has first and second opposable components 62 and 64. The first opposable component 62 has a chromatographic medium 66 with first and second ends 68 and 70. The chromatographic medium 66 has a detection zone 72 and, optionally, a control zone 74. The first opposable component has a first labeled specific binding partner applicator 76 and a second labeled specific binding partner applicator 78, each for applying a labeled specific binding partner for the analyte to the chromatographic medium. Typically, the first and second labeled specific binding partner applicators 76 and 78 each contain a labeled specific binding partner for the analyte in resolubilizable form; alternatively, a labeled specific binding partner can be applied to the first and second labeled specific binding partner applicators 76 and 78 during the performance of the assay. The first and second labeled specific binding partner applicators 76 and 78 are not in operable contact when the first and second opposable components are separated. Although the version of the device shown in FIG. 3 has two labeled specific binding partner applicators, more than two can be used; the illustration of two labeled specific binding partner applicators is only for convenience, and as many labeled specific binding partner applicators can be used as can be accommodated by the opposable components. The labeled specific binding partner applicator located furthest from the chromatographic medium can contain a reagent for extraction of the sample or other reagents for treatment of the sample before the sample is applied to the chromatographic medium and is intended for application of the sample.

The second opposable component 64 includes a wash liquid applicator 80 for application of a wash liquid, a first conductor 82, a second conductor 84, and an absorber 86. The first conductor 82 is placed in operable contact with the first and second sample preparation zones 76 and 78 when the opposable components are brought into opposition. The second conductor 84 is brought into contact with the first sample preparation zone 76 and the chromatographic medium 66 through its first end 68 when the opposable components are brought into opposition. The wash liquid applicator 80 is brought into operable contact with the second specific binding partner applicator 78 when the opposable components are brought into opposition. If there are more than two specific binding partner applicators, the wash liquid applicator is brought into operable contact with the specific binding partner applicator located furthest from the chromatographic medium. The absorber 86 is brought into operable contact with the chromatographic medium 66 through its second end 70 when the opposable components are brought into opposition.

The device 60 further comprises a hinge 88 for joining the first and second opposable components 62 and 64. The device also includes at least one aperture 90 for viewing of the chromatographic medium 66, including the detection zone 72, and if present, the control zone 74. The device can also include locks, such as engagers 92 and 94 and a gasket or sealing ridge 96, as described above.

In use, a sample is applied to the second labeled specific binding partner applicator 78 and a wash liquid is applied to the wash liquid applicator 80. The first and second opposable components 62 and 64 are then brought into opposition. The sample and resolubilized labeled specific binding partner, followed by the wash liquid, migrates through the chromatographic medium 66. This allows detection and/or determination of the analyte by detecting and/or measuring the labeled specific binding partner bound at the detection zone 72.

Figure 4:
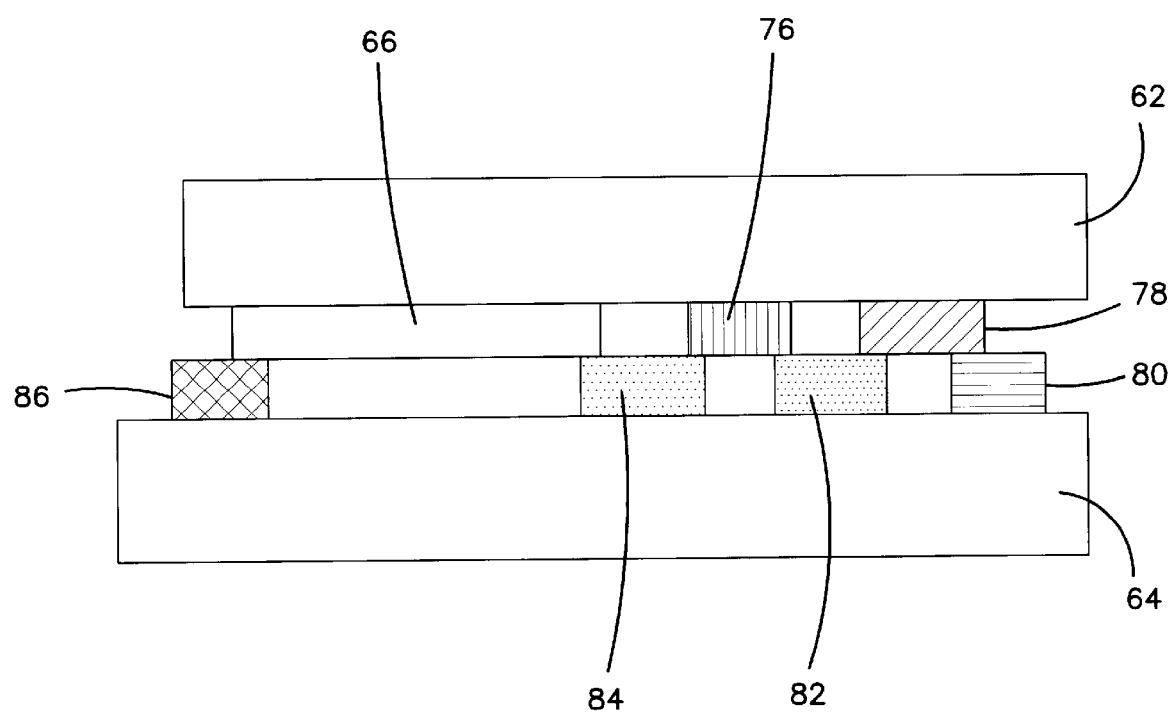
FIG. 4 is a schematic diagram showing the flow path of liquid through the device of FIG. 3.

In this embodiment of the device according to the present invention, the fluid flow path alternates between the first opposable component 62 and the second opposable component 64. The flow path is shown in FIG. 4.

3. Bridged Device for Use with Enzyme-Labeled Specific Binding Partners

Another embodiment of assay devices according to the present invention is a bridged device for use with an enzyme-labeled specific binding partner. In general, in these devices, the label of the labeled specific binding partner is a catalyst, preferably an enzyme.

In this embodiment, the first applicator contains a substance that participates in a reaction catalyzed by the catalyst to produce a detectable product. The substance can be a substrate, a coenzyme, or other cofactor. In any event, the result of the reaction is a detectable product. Preferably, this is an insoluble product that is deposited at the detection zone.

Figure 5:
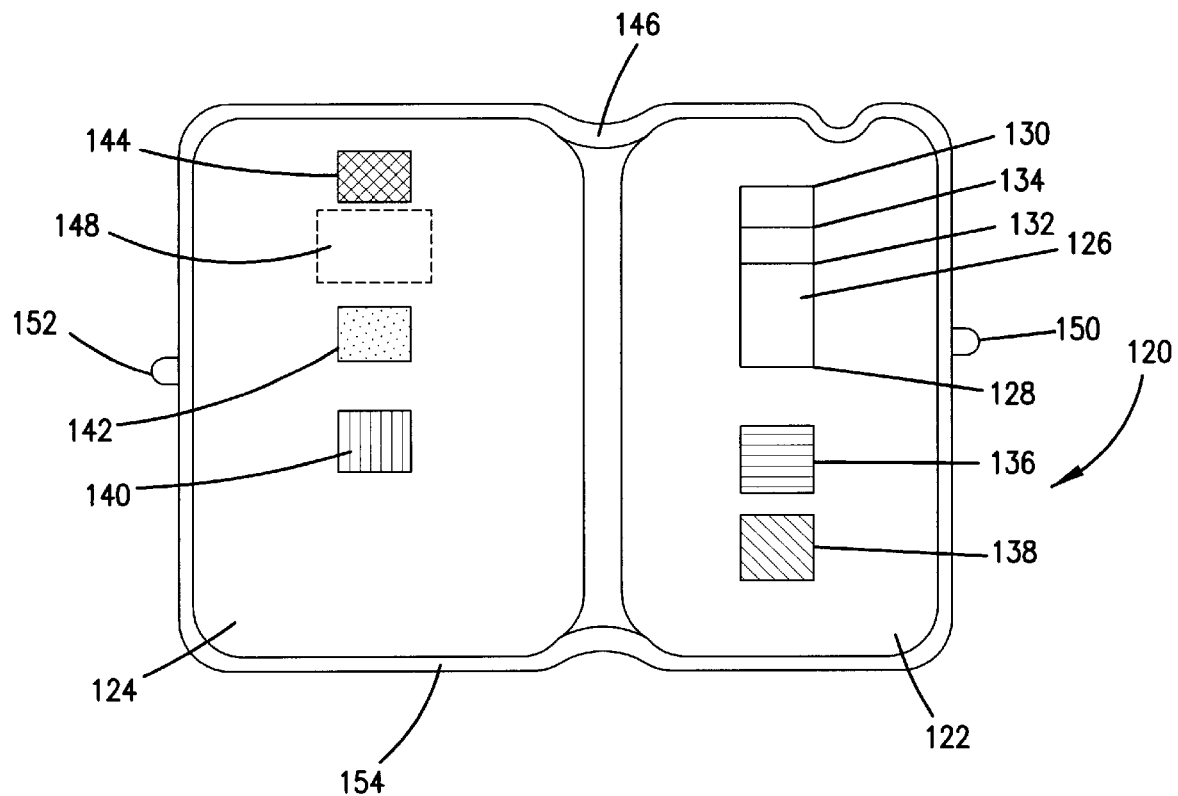
FIG. 5 is a drawing of a third embodiment of an assay device according to the present invention that uses a specific binding partner labeled with a catalyst.

This embodiment of the device is shown in FIG. 5. The device 120 includes first and second opposable components 122 and 124. The first opposable component 122 includes a chromatographic medium 126 with first and second ends 128 and 130, a detection zone 132, and, optionally, a control zone 134. The first opposable component 122 also contains a sample preparation zone 136 for receiving a sample to be assayed. The sample preparation zone 136 includes a catalyst-labeled specific binding partner for the analyte in resolubilizable form. The sample preparation zone 136 is separated from the chromatographic medium 126.

The first opposable component 122 also includes a first applicator 138 that contains a substance that participates in a reaction catalyzed by the catalyst to produce a detectable product. The first applicator 138 is separated on the first opposable component 122 from the chromatographic medium and the sample preparation zone.

The second opposable component 124 includes a second applicator 140 for application of a wash liquid, a conductor 142, and an absorber 144 separated from the conductor 142 and the second applicator 140. The device further includes a hinge 146 joining the first and second opposable components 122 and 124 and at least one aperture 148 that allows viewing of at least a portion of the chromatographic medium 126, including the detection zone 132, and if present, the control zone 134. The device 120 can further include engagers 150 and 152 such as locks and a gasket or sealing ridge 154.

When the first and second opposable components 122 and 124 are brought into opposition, the second applicator 140 is brought into operable contact with the sample preparation zone 136, the conductor 142 is brought into operable contact with the sample preparation zone 136 and the chromatographic medium 126 through its first end 128, and the absorber 144 is brought into operable contact with the chromatographic medium 126 through its second end 130.

In use, a sample is applied to the sample preparation zone 136, a wash liquid is applied to the second applicator 140, and a substrate catalyzed by the label is applied to the first applicator 138. The first and second opposable components 122 and 124 are then brought into opposition. This causes the wash liquid to be applied to the sample preparation zone 136. The user then allows the sample and the substrate or other substance participating in the reaction catalyzed by the catalyst of the label to migrate through the chromatographic medium for detection and/or determination of the analyte.

Figure 6:
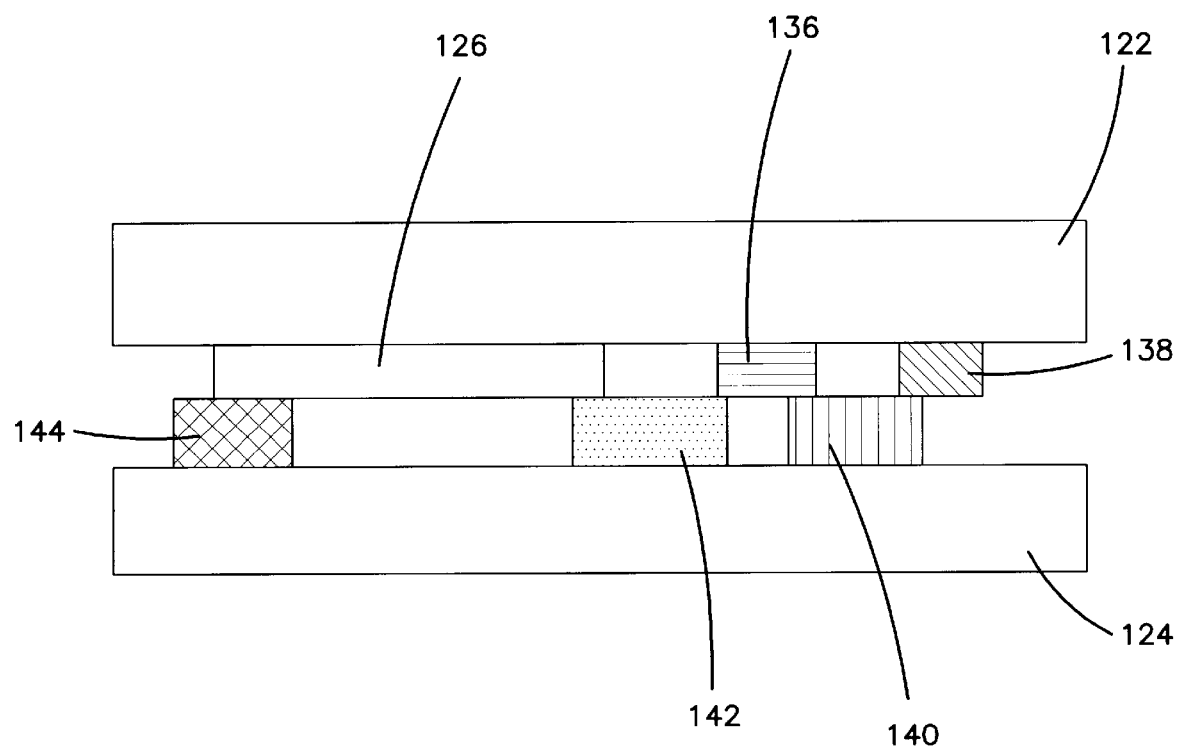
FIG. 6 is a schematic diagram showing the flow path of liquid through the device of FIG. 5.

In this embodiment of the device according to the present invention, the fluid flow path alternates between the first opposable component 122 and the second opposable component 124. The flow path is shown in FIG. 6.

Preferably, the catalyst is an enzyme. However, the catalyst can also be a nonenzymatic catalyst.

Enzymes for use as labels of specific binding partners are well known in the art. Such enzyme labels include, but are not limited to horseradish peroxidase, alkaline phosphatase, β-galactosidase, and glucose oxidase.

The use of such enzymes as labels for specific binding partners, particularly antibodies, is described in G. T. Hermanson, "Bioconjugate Techniques" (Academic Press, San Diego, 1996), pp. 630–638, incorporated herein by this reference.

Preferably, the enzyme is covalently linked to the antibody or other specific binding partner. Methods for such conjugation are also well known in the art and describe, for example in G. T. Hermanson, *Bioconjugate Techniques* (Academic Press, San Diego, 1996), pp. 460–487, incorporated herein by this reference. Typically, such cross-linking is performed by the use of reagents such as heterobifunctional reagents containing an amine-reactive NHS-ester on one end and a sulfhydryl-reactive maleimide group on the other end. Many such heterobifunctional reagents are known in the art. Other cross-linking reactions, such as cross-linking with glutaraldehyde or conjugation via reductive amination, can be performed and are well known in the art.

Preferably, the substance that participates in the reaction is a substrate that is converted to an insoluble product that is deposited at the detection zone as a result of the action of the catalyst. Such substrates include, for horseradish peroxidase, 4-chloro-1-naphthol, 3-amino-9-ethylcarbazole, and 3,3',4,4'-tetraaminobiphenyl. For alkaline phosphatase, a suitable substrate generating an insoluble product is bromochloroindolyl phosphate-nitro blue tetrazolium. Other suitable substrates are also well known in the art.

4. Device for Unidirectional Assay of Analyte in Blood Sample

Another aspect of the present invention is a device for unidirectional assay of an analyte in a blood sample.

Figure 7:
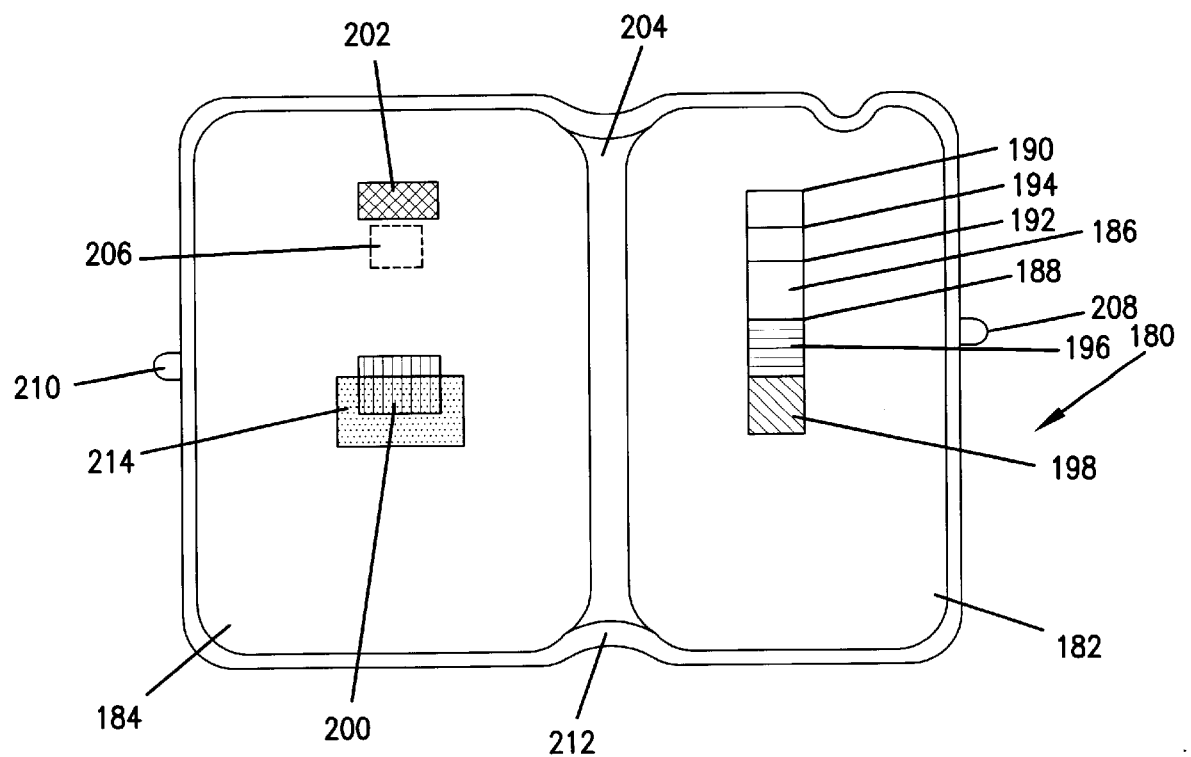
FIG. 7 is a drawing of a fourth embodiment of an assay device according to the present invention intended for use with a whole blood sample.

This device is shown in FIG. 7. The device 180 has first and second opposable components 182 and 184. The first opposable component 182 has a chromatographic medium 186 with first and second ends 188 and 190. The chromatographic medium 186 includes a detection zone 192, and, optionally, a control zone 194. The first opposable component 182 also includes a first applicator 196. The first applicator 196 contains a labeled specific binding partner for the analyte in resolubilizable form. The first applicator 196 is in operable contact with the chromatographic medium 186 through its first end 188. The first opposable component 182 further includes a sample preparation zone 198 that is in operable contact with the first applicator 196. The chromatographic medium 186, first applicator 196, and sample preparation zone 198 are arranged on the first opposable component 182 so that the first applicator 196 is between the sample preparation zone 198 and the chromatographic medium 186.

The second opposable component 184 includes a second applicator 200 for application of a wash liquid and an absorber 202. When the first and second opposable components 182 and 184 are brought into opposition, the second applicator 200 is brought into operable contact with the first applicator 196 to apply a wash liquid. The absorber 202 is brought into operable contact with the chromatographic medium 186 through its second end 190 to drive flow through the chromatographic medium 186 from its first end 188 to its second end 190. The first and second opposable components 182 and 184 are joined by a hinge 204. At least one of the first and second opposable components 182 and 184 has an aperture 206 for viewing of at least a portion of the chromatographic medium 186, including the detection zone 192, and if present, the control zone 194. The first and second opposable components 182 and 184 can include locks such as engagers 208 and 210 to hold the first and second opposable components 182 and 184 in opposition or in operable contact. The device 180 can also include a sealing ridge or gasket 212. Preferably, the device also includes a barrier 214, such as a clear, self-adhesive film, to prevent fluid flow between the second applicator 200 and the sample preparation zone 198.

In the operation of this embodiment, first a sample, typically a whole blood sample, is applied to the sample preparation zone 198. Preferably, the whole blood sample is applied to the center of the sample preparation zone 198. Preferably, a measured volume of a running buffer is then applied to the lower portion of the sample preparation zone 198, i.e., the portion farthest away from the chromatographic medium 186, to displace the plasma from the sample preparation zone 198 and to aid in resolubilizing the resolubilizable labeled specific binding partner in the first applicator 196. The sample then migrates into the first applicator 196 containing the resolubilizable labeled specific binding partner for the analyte. While the device 180 remains open, a wash liquid, which can be the same running buffer as applied to the sample preparation zone 198, is applied to the second applicator 200. When the sample and the resolubilized labeled specific binding partner reach the chromatographic medium 186, the device 180 is closed by bringing the first and second opposable components 182 and 184 into operable contact, causing the wash liquid to be applied to the first applicator 196. This allows clearing of the background in the chromatographic medium 186 to increase the sensitivity of the device.

The test sample to be assayed in this device is typically whole blood. However, the device can also advantageously be used for assay of other body fluids that may or may be suspected of containing blood cells, such as urine, cerebrospinal fluid, or other biological fluids that may contain blood. Even though the blood may be itself an indicator of an abnormal condition, its presence can interfere with the assay of various analytes by immunoassays or other specific binding assays.

The matrix of porous material permeable to the liquid portion of blood but capable of trapping the cellular components of blood can include, for example, phosphate buffered saline containing a detergent such as 0.1% Tween™ 20 and a chelating agent such as 0.15% EDTA.

Other methods for separating the cellular components of blood from the liquid portion of blood are known in the art and can be used in conjunction with the sample preparation zone 198.

Figure 8:
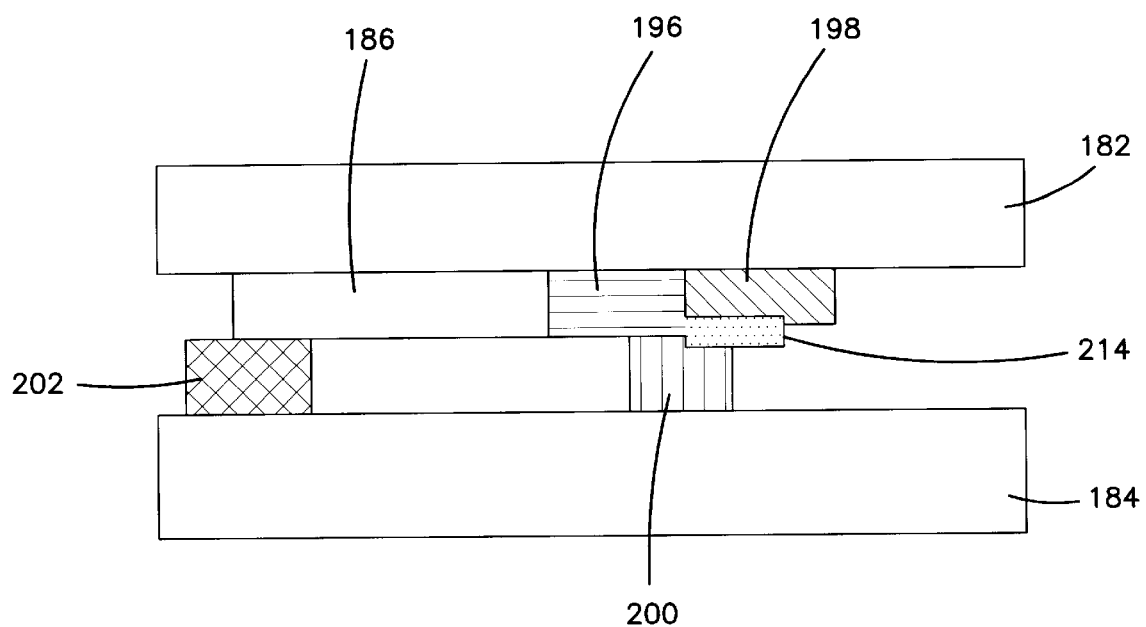
FIG. 8 is a schematic diagram showing the flow path of liquid through the device of FIG. 7.

In this embodiment of the device according to the present invention, the fluid flow path switches from the first opposable component 182 and the second opposable component 184. The flow path is shown in FIG. 8.

5. Multiplex Devices

The foregoing description of alternative embodiments of the present invention is directed to devices that are constructed to perform one assay. However, the same principles can be used to construct multiplex devices that can perform more than one assay on the same device.

Each of the embodiments shown above in Sections (C)(1) through (C)(4) can be used as the basis for a multiplex device. In multiplex devices according to the present invention, there are an equal number of elements located on the first opposable component and the second opposable component. Each pair of elements functions exactly as do the corresponding elements in a single-assay device. The term "corresponding" is used herein to refer to the elements that come into contact when the first and second opposable components of the device are brought into opposition or operable contact in such a multiplex device.

When multiple assays are performed simultaneously, the assays can be performed on the same analyte or different analytes. For example, the multiplex devices can be used to assay a number of different analytes in different aliquots of the same sample, or can be used to assay the same analyte in a number of different samples. This latter mode is particularly useful in assaying for a condition for which samples taken at different times from the same patient must be assayed for the analyte of interest, such as fecal occult blood. The presence of fecal occult blood is frequently determined by means of a series of stool samples taken once a day or at other intervals for a prescribed period. Alternatively, one or more of the assays can be used for controls or reference standards.

One embodiment of a multiplex device according to the present invention is based on the device of section (C)(1) and comprises:

(1) a first opposable component including:
 (a) a plurality of laterally separated sample preparation zones, each sample preparation zone for receiving a sample to be assayed; and
 (b) a plurality of laterally separated chromatographic media, each chromatographic medium having first and second ends and including therein a detection zone containing an immobilized specific binding partner for an analyte, each chromatographic medium being located in line with a sample preparation zone; and
(2) a second opposable component including:
 (a) a plurality of laterally separated conductors;
 (b) a plurality of laterally separated absorbers, each absorber in line with a conductor; and
 (c) a plurality of laterally separated applicators, each applicator being located in line with a conductor and an absorber.

When the first and second opposable components are brought into operable contact, each applicator is brought into operable contact with the corresponding sample preparation zone, each conductor is brought into operable contact with the corresponding sample preparation zone and with the corresponding chromatographic medium, and each absorber is brought into operable contact with the second end of the corresponding chromatographic medium.

Figure 9:
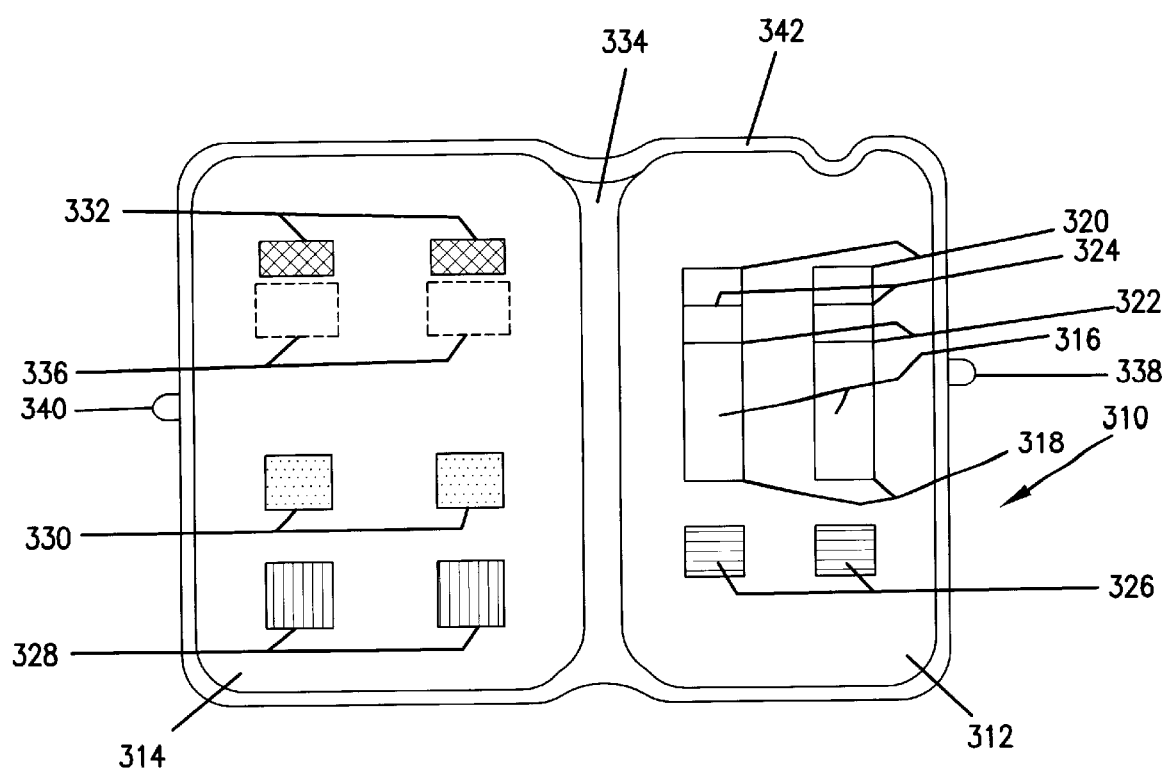
FIG. 9 is a diagram of an assay device according to the present invention for performing multiple assays within a single device.

This device is shown in FIG. 9. The device 310 is shown with two chromatographic media; however, such devices can be constructed with as many as 5 to 15 or more chromatographic media for the performance of a like number of assays. The device 310 has a first opposable component 312 and a second opposable component 314. The first opposable component 312 has two chromatographic media 316, each with a first end 318 and a second end 320. Each chromatographic medium 316 has a detection zone 322 and a control zone 324. Corresponding to each chromatographic medium 316 is a sample preparation zone 326, constructed as described above. Each chromatographic medium 316 and sample preparation zone 326 are located on the first opposable component 312 so that the chromatographic medium 316 and sample preparation zone 326 for the performance of each individual assay are in a linear arrangement.

The second opposable component 314 includes a plurality of laterally separated conductors 330, a plurality of laterally separated absorbers 332, each absorber 332 being located in line with a conductor 330, and a plurality of laterally separated applicators 328, each applicator 328 being located in line with an absorber 332 and a conductor 330. The first and second opposable components 312 and 314 are joined by a hinge 334, and at least one of the opposable components 312 and 314 has an aperture or apertures 336 for viewing the chromatographic media 316, including the detection zones 322 and the control zones 324, if present. Typically, the device further includes locks such as engagers 338 and 340 and a sealing ridge or gasket 342.

Another embodiment of a multiplex device according to the present invention is constructed according to the principles of the device in section (C)(2).

This device comprises:

(1) a first opposable component including:
 (a) a plurality of laterally separated chromatographic media as described above;
 (b) for each chromatographic medium, a plurality of labeled specific binding partner applicators for applying a labeled specific binding partner for an analyte to the chromatographic medium, the labeled specific binding partner applicator located farthest from the chromatographic medium for receiving a sample to be assayed, each chromatographic medium being located on the first opposable component in line with an equal number of labeled specific binding partner applicators; and
(2) a second opposable component including:
 (a) a plurality of laterally-separated wash liquid applicators, one applicator for each chromatographic medium;
 (b) a plurality of laterally-separated conductors, each conductor being located in line with an applicator, with there being at least as many conductors for each chromatographic medium as the number of labeled specific binding partner applicators minus one for each chromatographic medium; and
 (c) a plurality of laterally-separated absorbers, one absorber for each chromatographic medium, each absorber being located in line with a wash liquid applicator and a conductor.

When the first and second opposable components are brought into opposition, each wash liquid applicator is brought into operable contact with a corresponding labeled specific binding partner applicator. The labeled specific binding partner applicators with which the wash liquid applicators are brought into contact are those that are located the furthest from each chromatographic medium. Each conductor is brought into operable contact with either two corresponding labeled specific binding partner applicators or a corresponding labeled specific binding partner applicator and the first end of a corresponding chromatographic medium. Each absorber is brought into operable contact with the second end of a corresponding chromatographic medium.

Figure 10:
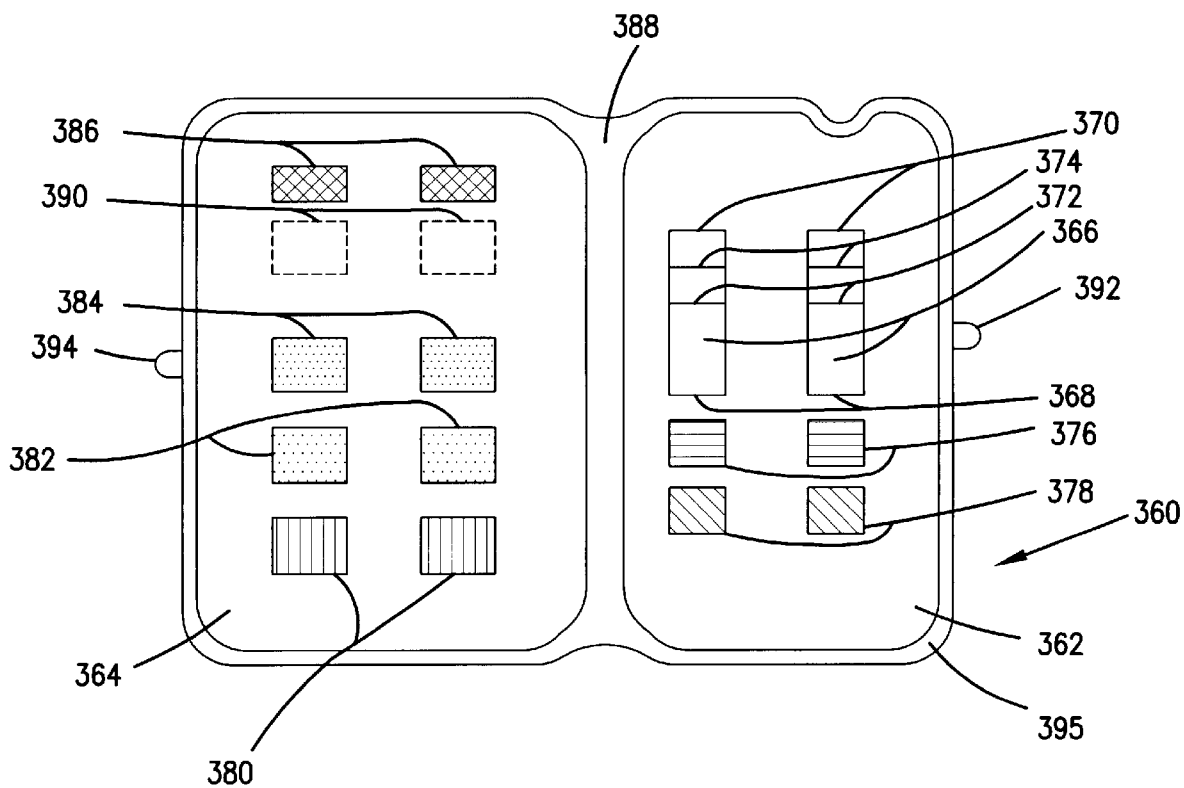
FIG. 10 is a diagram of another assay device for performing multiple assays within a single device, employing multiple sample preparation zones for each assay.

This device is shown in FIG. 10. The device 360 has first and second opposable components 362 and 364. The first opposable component 362 has a plurality of chromatographic media 366, each with first and second ends 368 and 370, a detection zone 372, and, optionally, a control zone 374. Each first opposable component 362 also has a plurality of first labeled specific binding partner applicators 376 and second labeled specific binding partner applicators 378, one for each chromatographic medium 366. (Although only two labeled specific binding partner applicators per chromatographic medium are shown in this example, more than two sample preparation zones can be used.) Each first labeled specific binding partner applicator 376 and second labeled specific binding partner applicator 378 is located in line with a chromatographic medium 366. Each second labeled specific binding partner applicator 378 is for receiving the sample to be assayed.

Each second opposable component 364 includes a plurality of wash liquid applicators 380, first conductors 382, second conductors 384, and absorbers 386. Each first conductor 382, second conductor 384, and absorber 386 is in line with a wash liquid applicator 380. Each wash liquid applicator 380, first conductor 382, second conductor 384, and absorber 386 corresponds to a chromatographic medium 366 on the first opposable component 362. The device 360 further includes a hinge 388 for joining the first and second opposable components 362 and 364, an aperture or apertures 390 for viewing of the chromatographic media 366 including the detection zones 372 and if present, the control zones 374, and, preferably, engagers such as locks 392 and 394 and a gasket or sealing ridge 396.

Another version of a multiplex assay device according to the present invention is particularly adapted for use with an enzyme-labeled specific binding partner for the analyte.

This device comprises:

(1) a first opposable component including:

(a) a plurality of laterally-separated chromatographic media as described above;

(b) a plurality of laterally-separated sample preparation zones, one for each chromatographic medium, each sample preparation zone including a specific binding partner for an analyte in a resolubilizable form labeled with a catalyst, each sample preparation zone being in line with a chromatographic medium; and (c) a plurality of first applicators, each first applicator containing a substrate that participates in a reaction catalyzed by the catalyst, the reaction forming a detectable product, each first applicator being in line with a chromatographic medium and a sample preparation zone; and (2) a second opposable component including:

(a) a plurality of laterally-separated second applicators, one second applicator for each chromatographic medium;

(b) a plurality of laterally-separated conductors, one conductor for each chromatographic medium, each conductor being in line with a second applicator; and (c) a plurality of laterally-separated absorbers, one absorber for each chromatographic medium, each absorber being in line with a second applicator and a conductor.

The first and second opposable components are configured so that bringing the first and second opposable components into operable contact causes each second applicator to come into operable contact with a corresponding first applicator and sample preparation zone. Bringing the first and second opposable components into operable contact also causes each conductor to come into operable contact with a corresponding sample preparation zone and a chromatographic medium via the first end of the chromatographic medium, and also causes each absorber to come into operable contact with a corresponding chromatographic medium via the second end of each chromatographic medium.

The general operation of this device is as described above in section (C) (3).

Figure 11:
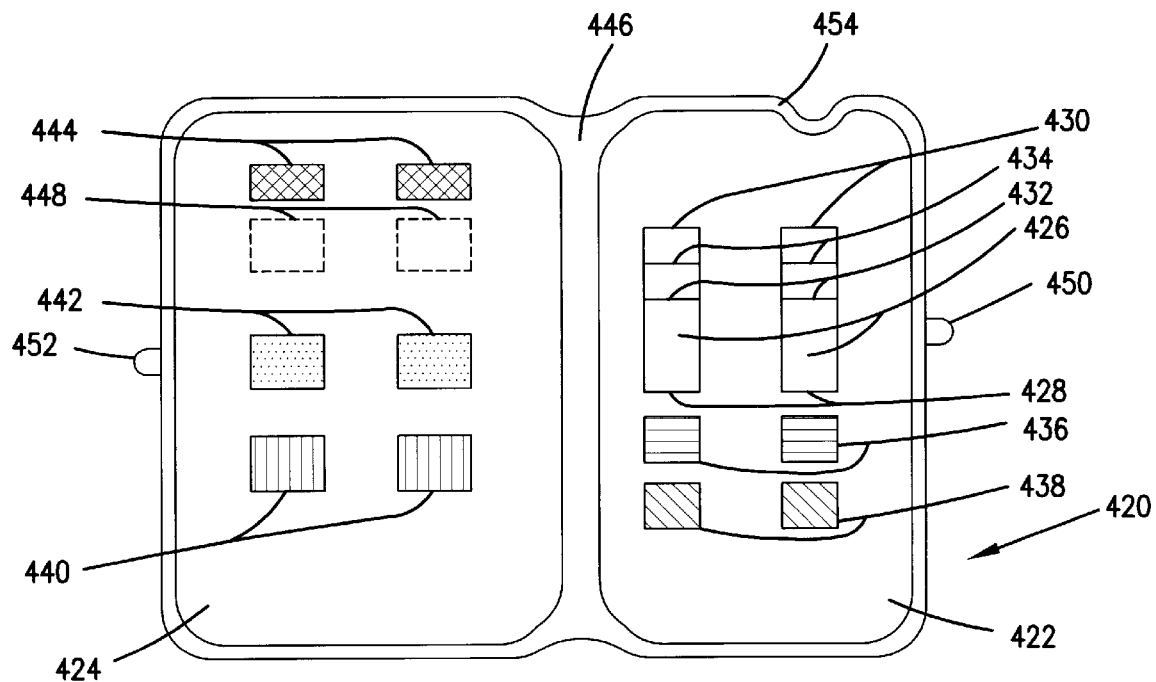
FIG. 11 is a diagram of another assay device for performing multiple assays within a single device, particularly suitable for use with a specific binding partner labeled by a catalyst.

This device is shown in FIG. 11. The device 420 includes first and second opposable components 422 and 424. Each first opposable component 422 includes a plurality of chromatographic media 426, each with first and second ends 428 and 430, a detection zone 432, and, optionally, a control zone 434. Each first opposable component also includes a plurality of sample preparation zones 436, one for each chromatographic medium 426. Each first opposable component 422 also includes a plurality of first applicators 438, one for each chromatographic medium 426. The first applicator 438 contain a substrate for the catalyst of the labeled specific binding partner that is located in the sample preparation zone 436.

The second opposable component 424 includes a plurality of second applicators 440, conductors 442, and absorbers 444, one for each chromatographic medium 426. The device 420 further includes a hinge 446, and an aperture or apertures 448 for viewing the chromatographic media 426, including the detection zones 432, and if present, the control zones 434. The device 420 preferably further includes engagers such as locks 450 and 452 and a sealing ridge or gasket 454.

The operation of this device is as described above in section (C) (3), using an enzyme label or other catalyst label.

Another multiplex device according to the present invention is particularly adapted to use with a sample of whole blood. This device is constructed according to the principles of the device described above in section (C)(4).

In general, this device comprises:

(1) a first opposable component including:

(a) a plurality of laterally-separated chromatographic media as described above;

(b) a plurality of laterally-separated first applicators, one first applicator for each chromatographic medium, each first applicator being in operable contact with the first end of a chromatographic medium; and (c) a plurality of laterally-separated sample preparation zones, each sample preparation zone being in operable contact with a corresponding first applicator; and (2) a second opposable component including:

(a) a plurality of laterally-separated second applicators, one for each chromatographic medium; and (b) a plurality of laterally-separated absorbers, one for each chromatographic medium, each absorber being in line with a second applicator.

Each sample preparation zone includes a matrix of porous material permeable to the liquid portion of blood but capable of trapping the cellular components of blood. The first and second opposable components are configured so that bringing the first and second opposable components into operable contact causes each second applicator to come into operable contact with the corresponding first applicator, and causes each absorber to come into operable contact with the corresponding chromatographic medium via the second end of the chromatographic medium.

Figure 12:
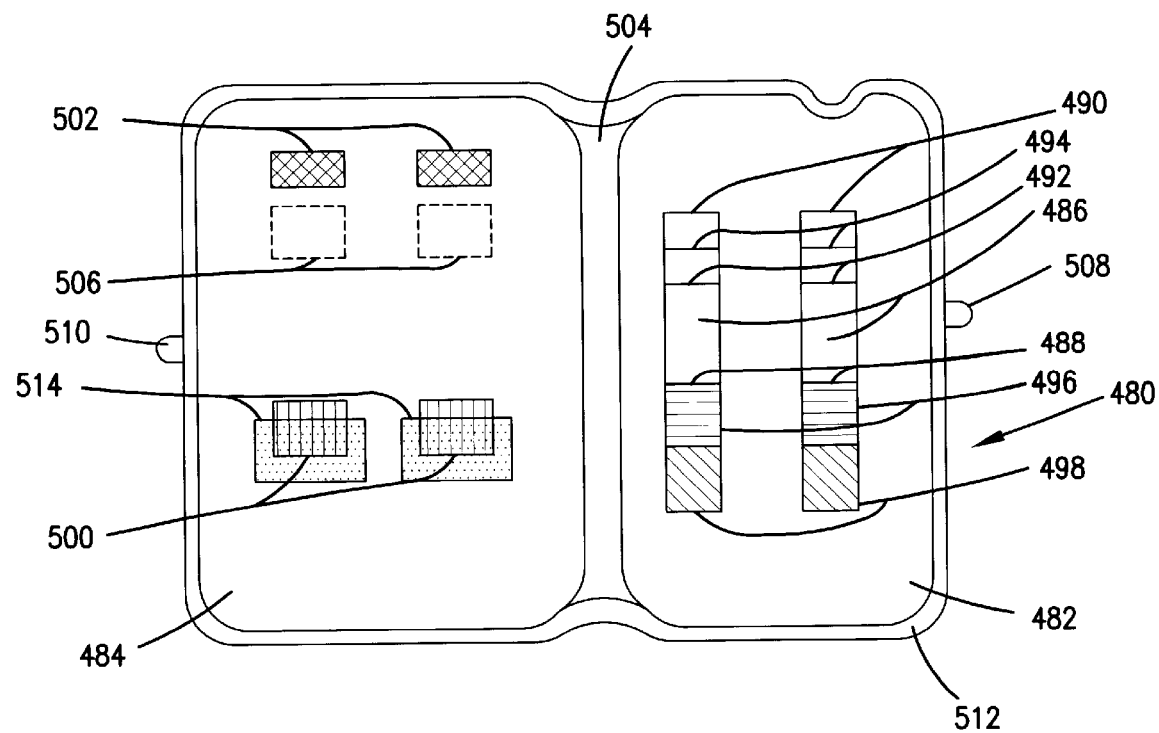
FIG. 12 is a diagram of another assay device for performing multiple assays within a single device, particularly suitable for use with whole blood samples.

This device is shown in FIG. 12. The device 480 has first and second opposable components 482 and 484. The first opposable component 482 has a plurality of chromatographic media 486, each with first and second ends 488 and 490, a detection zone 492, and, optionally, a control zone 494. Each first opposable component 482 has a plurality of first applicators 496, each in operable contact with the first end 488 of a corresponding chromatographic medium 486. Each first applicator 494 contains a labeled specific binding partner for the analyte. Each first opposable component 482 contains a plurality of sample preparation zones 498, one for each chromatographic medium 486. Each sample preparation zone 498 includes a matrix of porous material permeable to the liquid portion of blood but capable of trapping the cellular components of blood. The second opposable component 484 includes a plurality of second applicators 500 and a plurality of absorbers 502. The first and second opposable components 482 and 484 are joined by a hinge 504. The device 480 includes an aperture or apertures 506 for viewing the chromatographic media 486, including the detection zone 492, and if present, the control zone 494. The first and second opposable components 482 and 484 typically include locks such as engagers 508 and 510 as well as a gasket or sealing ridge 512, although these elements are not required. Preferably, the device also includes at least one barrier 514, such as a clear, self-adhesive film, to prevent fluid flow between the second applicator 500 and the sample preparation zone 498.

II. ANALYTES AND SPECIFIC BINDING PARTNERS FOR USE WITH ASSAY DEVICES

The analytes suitable for detection with an assay device according to the present invention include antigens, haptens and antibodies. Antigens detectable with the device include hemoglobin, Streptococcus A and B antigens, antigens specific for the protozoan parasite Giardia, and viral antigens, including antigens specific for HIV and the Australian antigen specific for hepatitis. Antibodies that can be assayed include antibodies to bacteria such as *Helicobacter pylori* and to viruses including HIV. Haptens detectable include haptens to which antibodies of sufficient specificity can be prepared.

Two antigens for which devices according to the present invention are particularly suitable are human hemoglobin and Streptococcus A antigen. The detection of human hemoglobin is clinically significant, because the presence of human hemoglobin in fecal material is a marker of intestinal or rectal bleeding, which is indicative of the presence of cancer in the gastrointestinal system or other pathogenic conditions. The detection of Streptococcus A antigen is also clinically significant, because streptococcal infections are fast moving and can be life-threatening.

If the analyte is an antigen or a hapten and a sandwich procedure is used, the first and second specific binding partners are preferably antibodies. In many applications, it is preferable that the first and second specific binding partners are antibodies to different epitopes on the analyte but this is not required in the case of an antigen that has multiple copies of the same epitope, such as a viral capsid made up of repetitive protein subunits. The antibodies can be polyclonal or monoclonal, and can be IgG, IgM, or IgA. In many applications, polyclonal antibodies are preferred, as their natural variability may allow more accurate detection in systems where antigenic polymorphisms exist or may exist. Where the analyte is a hapten and a sandwich assay procedure is used, it is strongly preferred that the first and second specific binding partners be antibodies to different epitopes; otherwise, there may be an undesirable competition reaction set up that may interfere with binding of a complex of the labeled specific binding partner and the analyte to the immobilized second specific binding partner. It is recognized that not all haptens are large enough to accommodate more than one epitope; however, some haptens, though not large enough to induce antigen formation efficiently when injected by themselves are nevertheless large enough that they possess more than one epitope. In cases where antibodies to more than one epitope for a hapten cannot be obtained, competitive assay procedures are generally preferred.

When the analyte is an antibody and a sandwich assay procedure is used, the labeled specific binding partner is typically a labeled antibody that binds to the analyte on the basis of species, class, or subclass (isotype) specificity. It is highly preferred that the labeled specific binding partner to an antibody analyte binds to the constant region of the antibody analyte, in order to prevent interference. When the analyte is an antibody, the unlabeled, immobilized specific binding partner is preferably an antigen or a hapten for which the antibody analyte is specific.

In some applications, it is desirable to employ indirect labeling. For example, in testing for Giardia antigen, an IgM antibody can be used that may be difficult to label directly. In that case, a secondary specific binding partner specific for the mobile first specific binding partner can be labeled. Typically, the labeled secondary specific binding partner binds to the antibody that is a first specific binding partner on the basis of species, class, or subclass specificity. As an alternative to the use of a secondary specific binding partner, the first specific binding partner can be conjugated to biotin and an avidin-conjugated or streptavidin-conjugated label can be used.

III. TEST KITS

Another aspect of the present invention is test kits. The test kit comprises, in separate containers:

(1) a chromatographic assay device according to the present invention;

(2) a wash liquid to be applied to the appropriate applicator on the second opposable component; and, optionally, (3) any additional reagents for treating or extracting the sample.

Components required in (2) and (3) are packaged separately and can be in liquid or solid form (freeze-dried, crystallized, precipitated, or aggregated). If the latter, they are resolubilized by the user, typically with distilled or purified water, with physiological saline, or with a buffer solution.

Still other variations of test devices according to the present invention are possible. For example, any of the two-component devices described can have a cover hingedly attached to one of the opposable components. This cover can have an aperture cut therein to allow viewing of at least a portion of the chromatographic medium.

EXAMPLES

The invention is illustrated by the following Examples. These examples are for illustrative purposes only and are not to be construed as limiting the scope of the invention in any manner.

Example 1

Unidirectional Assay Device for Detection of Antigen in Whole Blood

The assay device described in this example is intended for the detection of an antigen in a whole blood sample. For the purposes of this example, the analyte to be assayed is described as the Australia antigen of hepatitis virus. This analyte is chosen because it is medically important and can be found in blood; however, the same construction and principles apply for other analytes.

Figure 13:
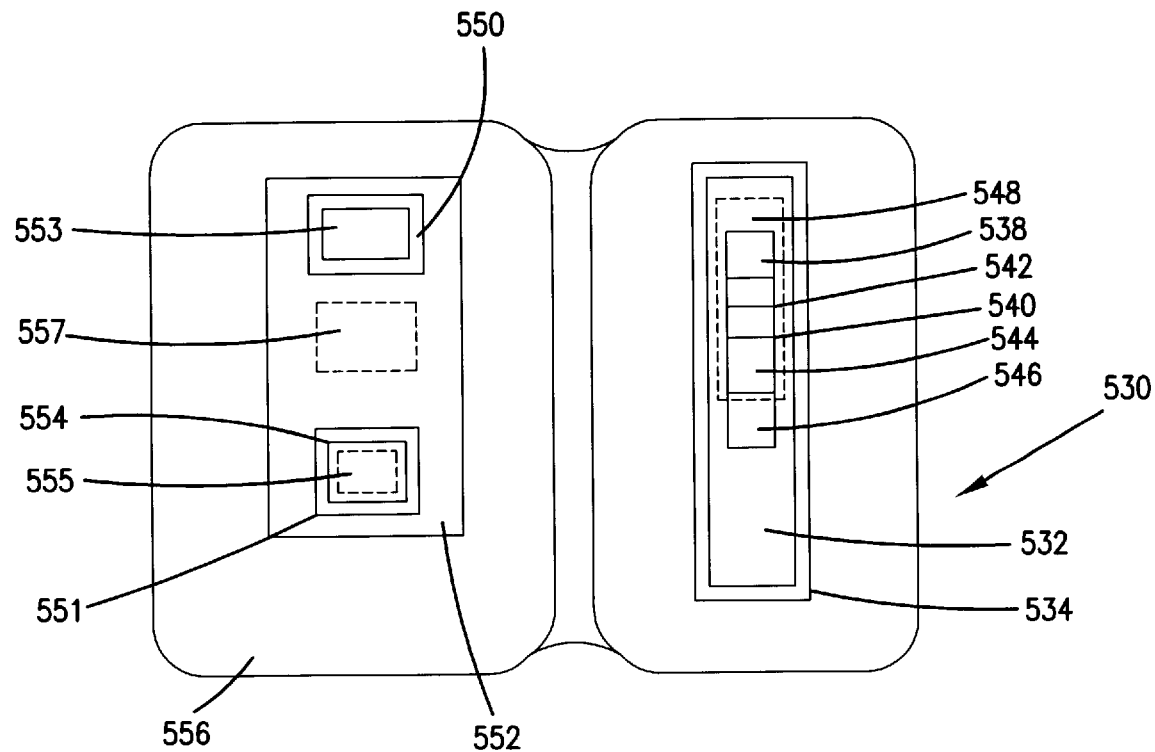
FIG. 13 is a diagram of the whole blood assay device of Example 1, showing details of assembly.

The construction of the assay device 530 is shown in FIG. 13. An adhesive film 532 (3M Corporation, 2 in.×12 in.) is placed down the center of a clear plastic support 534. A 1 in.×12 in. portion of the adhesive film 532 is exposed by removing a protective liner (not shown). A chromatographic medium 538 or nitrocellulose membrane (0.886 in.×12 in.) is secured to the exposed adhesive. A detection zone 540 has a zone of antibody specific for the analyte, such as rabbit anti-Australia antigen antibody, and is applied to the nitrocellulose membrane 538 approximately 0.25 in. from the lower margin of the membrane. A control zone 542 has a zone of antibody that is specific for the labeled specific binding partner to the analyte. It can be, for example, goat anti-rabbit immunoglobulin G if the label specific binding partner to the analyte is rabbit anti-Australia antigen immunoglobin G. The control zone 542 is applied about 0.375 in. from the lower margin of the membrane. A first applicator 544 (Ahlstrom Filtration, Holly Springs, Pa.), (0.5 in.×12 in.) is saturated with a labeled specific binding partner to the analyte, such as gold-labeled rabbit anti-Australia antigen antibody. The conjugate pad is allowed to dry. A sample preparation zone 546 or sample pad (Ahlstrom, 0.75 in.×12 in.) is treated to facilitate plasma separation by adding phosphate buffered saline containing 0.1% Tween 20 and 0.15% EDTA.

The test strip is assembled as follows: The remaining adhesive protective liner is removed. The dried conjugate pad is applied to the exposed adhesive such that a juncture of approximately 0.0625 in. is formed with the nitrocellulose membrane. The treated sample pad is applied to the remaining exposed adhesive such that a juncture of approximately 0.0625 in. is formed with the conjugate pad. A clear self-adhesive film 548 (Flexcon, 0.625 in.'12 in.) is placed over the nitrocellulose membrane, positioned to overlap the conjugate pad material by approximately 0.0625 in. The assembled test strip subassembly is then cut into 0.25 in. widths.

The second applicator, also known as a reagent/wash pad, is prepared as follows: Two parallel strips of adhesive film 550 and 551 (3M Corp., 0.5 in.×12 in.) are applied to a sheet of clear plastic support 552 (4 in.×12 in.) at a distance of approximately 0.75 in., and the protective liners are removed. Absorbents 553 and 554 (Ahlstrom, 0.5 in.×12 in.) are secured to the plastic support by the adhesive film. A clear, self-adhesive film 555 (Flexcon, 0.625 in.×12 in.) is placed over one absorbent strip such that an exposed margin of approximately 0.0625 in. is adjacent to the second absorbent strip. The reagent/wash pad subassembly is cut into 0.375 in. widths.

For assembly of the test device, the test strip and reagent/wash pad subassemblies are secured as illustrated to the housing 556 by means of an adhesive film (3M Corp., 0.25 in.×2 in.) (not shown). A viewing window or aperture 557 is cut in one of the portions of the housing 560.

In the operation of the device a whole blood sample is applied to the specimen pad and the plasma separated. Plasma is drawn out of the specimen pad into the conjugate pad. As the plasma enters the conjugate pad, the dry conjugate is reconstituted and the liquid front continue to migrate into the nitrocellulose membrane. The device is then closed. Closure of the device results in: (1) an absorbent pad contacting the top of the chromatographic membrane; and (2) a partially saturated wash pad contacting the lower margin of the conjugate pad. The flow of liquid from the wash pad results in displacement of the conjugate and clearance of the chromatographic medium to reduce the background. If analyte is present in the sample, the analyte reacts with the resolubilized conjugate and the conjugate-analyte complex is captured at the detection zone, i.e., the zone of immobilized antibodies specific for the analyte. Excess conjugate is captured at the second, control zone.

In the use of this device, a whole blood specimen (0.08 ml.) is applied to the center of the specimen pad, and the plasma is allowed to separate. Alternatively, serum or plasma can be directly added to the specimen pad. One drop (0.025 ml.) of running buffer, such as phosphate buffered saline, is applied to the lower portion of the specimen pad, displacing the plasma from the specimen pad and reconstituting the dried conjugate. The liquid front of the reconstituted conjugate is then allowed to flow onto the nitrocellulose membrane. Running buffer is applied to the exposed margin of the wash pad. A sufficient volume (0.075 ml.–0.125 ml.) is applied so that the wash pad is sufficiently moistened, but not saturated. The test housing is closed and sealed by means of an adhesive strip along the margin of the test housing. The results are interpreted through a viewing window in the test housing. Upon closing the test housing, the absorbent pad is brought into contact with the top of the nitrocellulose membrane and the wash pad is brought into contact with the lower portion of the conjugate pad. A positive test results in the development of two pink-purple lines at both the control and detection zones and a negative test results in the development of a single pink-purple line at the control zone in the upper portion of the viewing window.

Example 2

Bridged Device with Single Sample Preparation Zone

Figure 14:
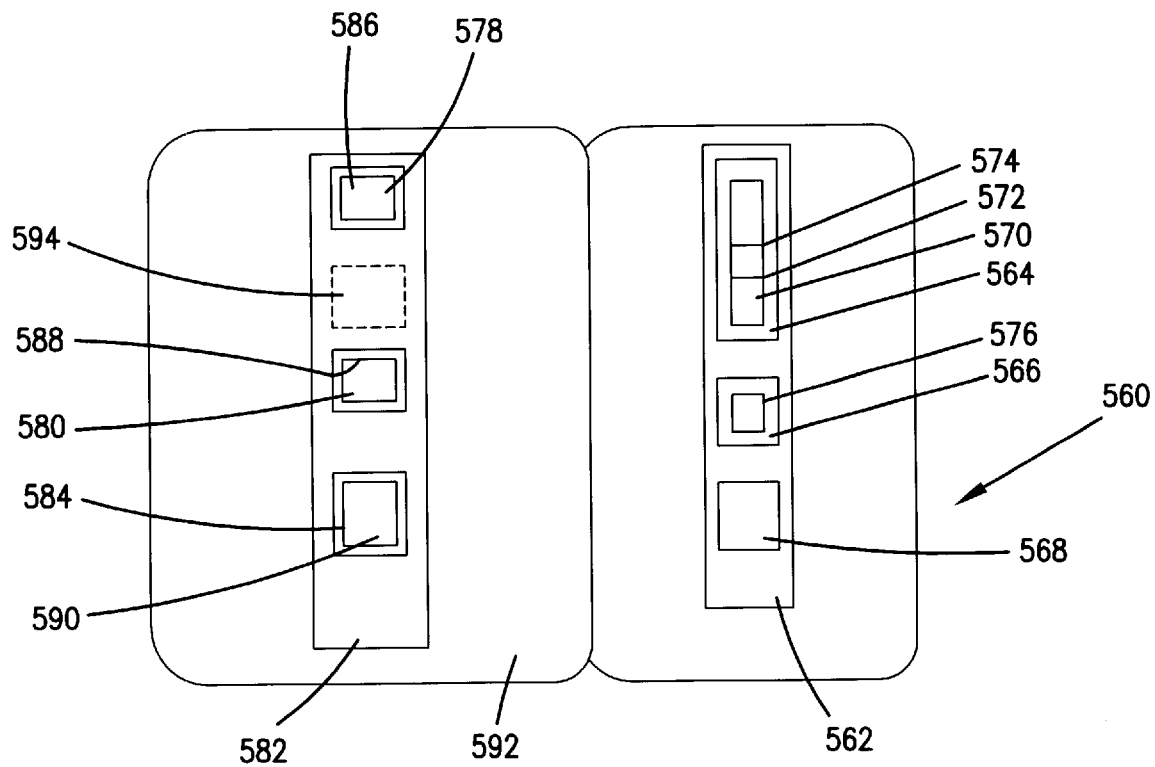
FIG. 14 is a diagram of the single bridge assay device of Example 2, showing details of assembly.

Another example is a bridged device with a single sample preparation zone. The device 560 is shown in FIG. 14. An adhesive film 562 (3M Corp., 0.75 in.×12 in.) is placed on a clear plastic support 564 (4 in.×12 in.). Maintaining a spacing of approximately 0.1875 in., a second adhesive film 566 (0.5 in.'12 in. each) is applied parallel to the first adhesive film 562. A chromatographic medium or nitrocellulose membrane 570 (0.888 in.×12 in.) is secured to the first adhesive film 562 (0.75 in.). A detection zone 572 of antibody specific for the analyte, such as rabbit anti-Australia antigen antibody, is applied to the nitrocellulose membrane approximately 0.25 in. from the lower margin of the membrane. A second, control, zone 574, which is specific for the labeled specific binding partner for the antibody, such as goat anti-rabbit immunoglobulin G antibody when the labeled specific binding partner for the analyte is gold-labeled rabbit anti-Australia antigen IgG, is applied to the nitrocellulose membrane approximately 0.375 in. from the lower margin. A first applicator or conjugate/specimen pad 576 (Ahlstrom, 0.5 in.×12 in.) is saturated with conjugate solution, i.e., gold-labeled rabbit anti-Australia antigen antibody, and dried.

The test strip is assembled as follows: The dried conjugate/specimen pad is applied to the exposed adhesive, maintaining the 0.1875 in. spacing with the nitrocellulose membrane. The assembled test strip subassembly is then cut into 0.25 in. widths.

For the preparation of the absorber, the conductor, and the second applicator, two parallel strips of adhesive film 578 and 580 (3M Corp., 0.5 in.×12 in.) are applied to a second sheet of clear plastic support 582 (4 in.×12 in.) spaced approximately 1.375 in. apart. A third strip of adhesive film 584 (3M Corp., 0.375 in.×12 in.) is applied to the support 582, approximately 0.75 in. from and parallel to one of the previously applied films. An absorber 586 (Ahlstrom, 0.5 in.×12 in.) is secured to an outer strip of the exposed adhesive. A conductor 588 (Ahlstrom, 0.375 in.×12 in.) is secured to the center strip of exposed adhesive. A second applicator 590 (Ahlstrom, 0.5 in.×12 in.) is secured to the remaining strip of exposed adhesive. The absorbent/bridge/chase pad subassembly is cut into 0.25 in. widths.

For test pad assembly, the subassemblies are secured as illustrated to the housing 592 by means of an adhesive film (3M Corp., 0.25 in.×2 in.) (not shown). A viewing window or aperture 594 is cut in one of the portions of the housing 592.

In the operation of this device, a sample is applied to the conjugate/specimen pad, and the dried conjugate is resolubilized. At a predetermined time after application of the sample, the device is closed. Closure of the device results in an absorbent pad contacting the top of the chromatographic medium, and a partially saturated chase pad contacting the lower margin of the sample pad. The bridge pad or conductor completes the flow path, allowing liquid to flow onto the chromatographic medium. If analyte is present in the specimen, it first reacts with the conjugate, i.e., the labeled specific binding partner for the analyte, and the conjugate-analyte complex is captured at the zone of immobilized antibody specific for the analyte, i.e., the detection zone 572. Excess labeled antibody specific for the analyte is captured at the second, control zone 574.

In use, a specimen is applied to the center of the specimen/conjugate pad and the component is allowed to react. Running buffer is applied to the exposed margins of the chase pad. A sufficient volume (0.075 to 0.100 ml.) of buffer is to be applied so that the pad is partially saturated. The housing is closed and sealed by means of an adhesive strip along the margin of the test housing and the results are interpreted through the viewing window. A positive test will result in the development of two pink-purple lines at the detection and control zone. A negative test will result in the development of a single pink-purple line in the upper portion of the viewing window at the control zone.

Example 3

Bridged Device With Multiple Sample Preparation Zones

Figure 15:
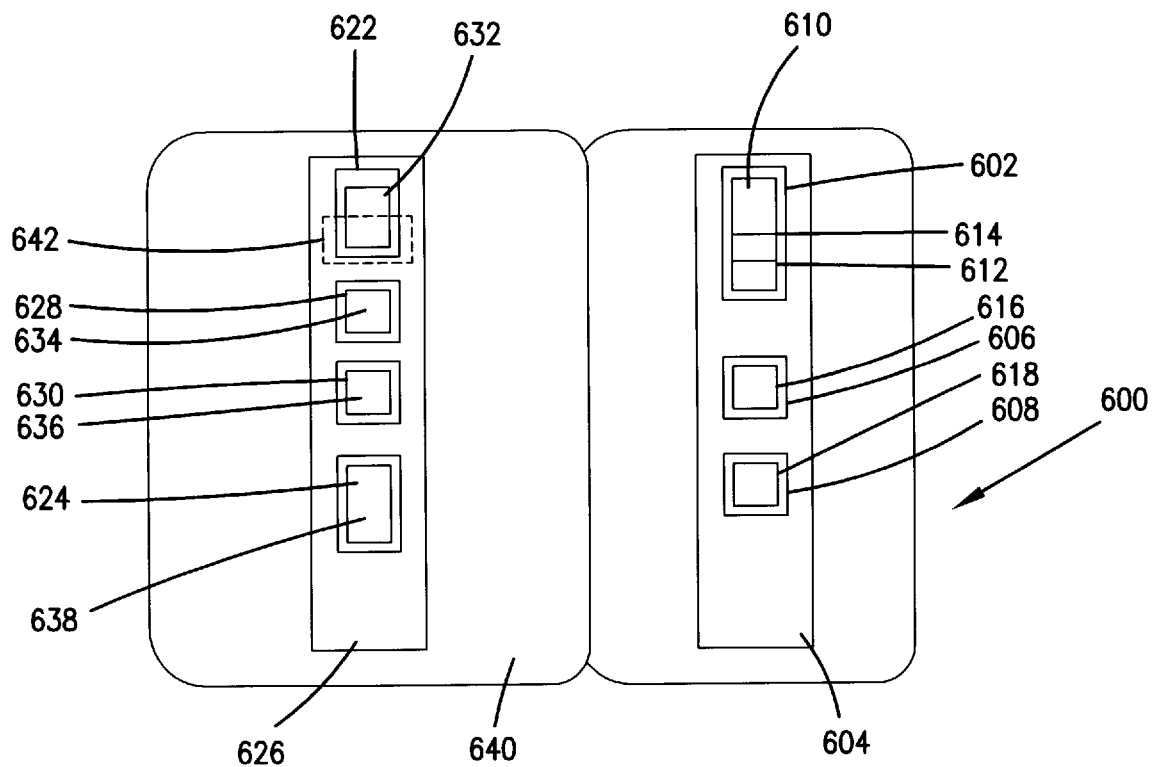
FIG. 15 is a diagram of the multiple bridged assay device of Example 3, showing details of assembly.

Another example of the device is one that employs multiple sample preparation zones, each containing a labeled specific binding partner to the analyte ("conjugate"). This device 600 is shown in FIG. 15. A first adhesive film 602 (3M Corp., 0.75 in.×12 in.) is placed on a clear plastic support 604 (4 in.×12 in.). A second and third adhesive film 606 and 608 (each 0.5 in.×12 in.) are applied parallel to the first adhesive film 602, maintaining a spacing of approximately 0.1875 in. A nitrocellulose membrane or chromatographic medium 610 (0.886 in.×12 in.) is secured to the first adhesive film (the 0.75 in. adhesive film). A detection zone of anti-analyte antibody 612, such as rabbit anti-Australia antigen antibody, is applied to the nitrocellulose membrane approximately 0.25 in. from the lower margin of the membrane. A second, control zone 614 of antibody that is specific for the labeled specific binding partner is applied to the nitrocellulose membrane or chromatographic medium 610 approximately 0.375 in. from the lower margin of the chromatography membrane. A sample preparation zone 616 (Ahlstrom, 0.5 in.×12 in.) is saturated with conjugate solution, i.e., gold-labeled rabbit anti-Australia antigen, and dried. A second pad or labeled specific binding partner applicator 618 is similarly treated with conjugate, i.e., gold-labeled rabbit anti-Australia antigen antibody. Alternatively, the second pad or labeled specific binding partner applicator 618 could be treated with a different conjugate to allow a second binding reaction by a different means or binding site.

The test strip is assembled as follows: The dried sample preparation zone 616 and labeled specific binding partner applicator 618 are applied to the exposed adhesive, maintaining the 0.1875 in. spacing. The assembled test strip subassembly is cut into 0.25 in. widths. For the preparation of the remaining components of the test device including the absorber, the applicator, and the two conductors, two parallel strips of adhesive film 622 and 624 (3M Corp., 0.5 in.×12 in.) are applied to a sheet of clear plastic support 626 (4 in.×12 in.) spaced approximately 1.625 in. Two parallel adhesive strips 628 and 630 (0.375 in.×12 in.) located between the previous strips, are applied to the support. One strip is spaced approximately 0.50 in. from one of the previously applied films. The remaining adhesive strip is applied parallel to and at a distance of approximately 0.8125 in. from the same strip.

An absorber 632 (Ahlstrom, 0.825 in.×12 in.) is secured to an outer strip of exposed adhesive. Conductors 634 and 636 (Ahlstrom, 0.375 in.×12 in.) are secured to each of the inner strips of adhesive. An applicator 638 for a wash fluid (Ahlstrom, 0.5 in.×12 in.) is secured to the remaining strip of exposed adhesive. The absorbent/bridge/chase pad subassembly is cut into 0.25 in. widths. For the assembly of the test device, the subassemblies are secured, as indicated, to the housing 640 by means of an adhesive film (3M Corp., 0.25 in.×2 in.) (not shown). A viewing window or aperture 642 is cut in one of the portions of the housing 640.

The principle of this format is essentially the same as that of the format with the single bridge pad or conductor. In the double bridge format, however, two bridge pads (conductors) and two reaction pads (elements containing labeled specific binding partner to the analyte) are employed. A sample is applied to the conjugate/specimen pad and the dried conjugate is reconstituted. After a predetermined time interval, the device is closed. Closure of the device results in an absorber contacting the top of the chromatographic medium and a partially saturated applicator for wash fluid contacting the lower margin of the sample/conjugate pad. Conductors or bridge pads complete the flow path, allowing liquid to flow from the conjugate/specimen pad onto the labeled specific binding partner applicator and finally onto the chromatographic medium. If analyte is present in the specimen, it first reacts with the conjugates, i.e., the labeled specific binding partners for the analyte, and the analyte-labeled specific binding partner complexes are captured at the zone of immobilized antibodies specific for the analyte. Excess conjugate is captured at the second zone.

This format can be used with enzyme labeling systems, in which case the applicator (wash pad) can be partially saturated with a suitable substrate and detection reagent for an enzyme.

In use of this format, a specimen (0.08 ml.) is applied to the center of the sample preparation zone (specimen/conjugate pad) and the components are allowed to react. Running buffer is applied to the exposed margin of the applicator (wash pad). A sufficient volume (0.075–0.100 ml.) is applied such that the wash pad is sufficiently moistened, but not saturated. The test housing is closed and sealed by means of an adhesive strip along the margin of the test housing. Results are interpreted through a viewing window. A positive test results in the development of two pink-purple lines and a negative test results in the development of a single pink-purple line in the upper portion of the viewing window.

ADVANTAGES OF THE INVENTION

Chromatographic assay devices according to the present invention provide an advantage in being constructed of opposable elements. The use of opposable elements provides great versatility, as it permits the performance of reactions in a number of different sequences. This is possible because the use of such opposable elements allows the delivery of reagents to precisely defined regions of a test strip or other reaction component. The use of opposable elements also provides optimum performance with minimum consumption of reagents by insuring that reagents are not wasted by being sequestered in dead volumes of apparatus. The use of opposable components also provides optimum containment of possibly contaminated blood samples, such as those containing HIV or hepatitis virus.

Another advantage of assay devices according to the present invention lies in the ability of the devices to use pressure to drive fluids from one opposable component to another and through the chromatographic medium and the control of pressure applied so that is optimum for each assay to be carried out. This accelerates the assay process and allows the performance of operations such as extraction within the assay device. It also reduces the dead volume of reagents remaining in components, allowing the use of smaller samples and smaller quantities of expensive or hard-to-purify reagents such as labeled antibodies.

Additionally, chromatographic assay devices according to the present invention allow the rapid and accurate detection of clinically important analytes, such as Australia antigen specific for hepatitis, Streptococcus A and B antigen and antibody to *Helicobacter pylori*. The construction of the devices allows more even application of the samples to the chromatographic medium, and reduces interference that might otherwise be introduced by particulates or colored samples. Additionally, the devices provide for an efficient unidirectional assay of analytes in whole blood.

The use of colloidal metal labels in a resolubilizable form provides extremely rapid kinetics of labeling and allows substantially complete formation of binary analyte-label complexes before the sample is applied to the chromatographic medium. This aids in the separation of contaminants and improves the performance of the assay. Additionally, the construction and arrangement of the housing of the device aids in the performance of the assay by assuring the withdrawal of excess immunoglobulin-containing sample which could otherwise create interference.

Extraction of biological samples such as blood, sputum, or feces can be performed directly in the device, reducing the quantity of contaminated material that must be disposed and reducing the likelihood of accidental infection of physicians, technicians, or the public by such contaminated material.

Test methods using the device as according to the present invention have a wide dynamic range and are particularly suitable for the assay of analytes in whole blood samples, increasing the quantity of sample reaching the detection zone by the use of a unidirectional assay and therefore increasing the sensitivity of the assay.

Additionally, the present invention allows for any desired length of preincubation of the reactants, and provides more homogeneous mixing of the analyte and label specific binding partner.

Although the present invention has been described in considerable detail, with reference to certain preferred versions thereof, other versions and embodiments are possible. These versions include other arrangements of two-component assay devices that operate by the basic principles described herein and utilize any of: (i) in situ extraction of the sample; (ii) resolubilization of a labeled specific binding partner and rapid binding to analyte; (iii) arrangement of the chromatographic medium and absorber to remove excess sample that could otherwise create interference; and (iv) application of a wash liquid to reduce the background in the chromatographic medium.

In particular, the device as according to the present invention can be adapted to make use of radial or circumferential flow through a chromatographic medium rather than linear flow. The present invention further encompasses variations in which the two components of the device are not held in a permanently fixed arrangement, but can be separated and brought together to perform the assay, such as by electrical or magnetic forces or by using a separable fastener such as a hook-and-eye fabric, for example Velcro™. Therefore, the scope of the invention is determined by the following claims.

I claim:

1. A chromatographic assay device for detection and/or determination of an analyte comprising:
    (a) a first opposable component including:
        (i) a sample preparation zone for receiving a sample to be assayed; and
        (ii) a chromatographic medium having first and second ends and having a detection zone containing an immobilized specific binding partner for the analyte, the chromatographic medium being separated from the sample preparation zone on the first opposable component; and
    (b) a second opposable component including:
        (i) a conductor;
        (ii) an absorber separated from the conductor; and
        (iii) an applicator separated on the second opposable component from the conductor and the absorber; wherein the first and second opposable components are configured so that bringing the first and second opposable components into operable contact results in the absorber coming into operable contact with the second end of the chromatographic medium, the conductor coming into operable contact with the sample preparation zone and the first end of the chromatographic medium, and in the applicator coming into operable contact with the sample preparation zone so that the sample preparation zone bridges the applicator and the conductor, and so that the chromatographic medium bridges the conductor and the absorber.

2. The chromatographic assay device of claim 1 wherein the sample preparation zone, the conductor, or both include a labeled specific binding partner for the analyte in resolubilizable form.

3. The chromatographic assay device of claim 1 wherein the sample preparation zone contains at least one reagent for treatment of the sample before the sample is applied to the chromatographic medium.

4. The chromatographic assay device of claim 3 wherein the reagent for treatment of the sample is a extraction reagent to extract analyte from the sample.

5. The chromatographic assay device of claim 2 wherein the label of the labeled specific binding partner is a visible label.

6. The chromatographic assay device of claim 1 wherein the chromatographic medium further includes a control zone separate from the detection zone.

7. The chromatographic assay device of claim 6 wherein the control zone contains analyte immobilized thereto.

8. The chromatographic assay device of claim 1 wherein at least one of the first and second opposable components includes an aperture therein for viewing of at least a portion of the chromatographic medium.

9. A test kit comprising, packaged in separate containers:
    (a) the assay device of claim 1; and
    (b) a wash liquid for application to the applicator of the assay device.

10. A method for detecting and/or determining an analyte in a sample comprising the steps of:
    (a) applying the sample to the sample preparation zone of the chromatographic assay device of claim 1;
    (b) applying a wash liquid to the applicator of the chromatographic assay device;

(c) bringing the first and second opposable components of the assay device into opposition;

(d) allowing the sample and the resolubilized labeled specific binding partner to move through at least a portion of the chromatographic medium including the detection zone, followed by the wash liquid from the applicator, so that the detection reagent give a detectable indication of the presence and/or quantity of the analyte; and (e) observing and/or measuring the labeled specific binding partner at the detection zone in order to detect and/or determine the analyte.

11. The method of claim 10 wherein the detectable label is a visually detectable label and the step of observing and/or measuring the labeled specific binding partner bound at the detection zone comprises visually observing the labeled specific binding partner.

12. A chromatographic assay device for detection and/or determination of an analyte comprising:

(a) a first opposable component including:
   (i) a plurality of labeled specific binding partner applicators, each labeled specific binding partner applicator for applying a labeled specific binding partner for the analyte to the chromatographic medium; and
   (ii) a chromatographic medium having first and second ends and including a detection zone containing an immobilized specific binding partner for the analyte, the chromatographic medium being separated from the labeled specific binding partner applicators on the first opposable component, at least one of the labeled specific binding partner applicators for receiving a sample to be assayed; and (b) a second opposable component including;
   (i) at least one conductor, with there being at least as many conductors as the number of labeled specific binding partner applicators on the first opposable component minus one, the conductors being located on the second opposable component such that, when the first and second opposable component are brought into operable contact, one conductor is in operable contact with a labeled specific binding partner applicator and the chromatographic medium and the other conductors are in operable contact with two labeled specific binding partner applicators;
   (ii) an absorber separated from the conductors on the second opposable components; and
   (iii) a wash liquid applicator separated on the second opposable component from the conductors and absorber; wherein bringing the first and second opposable components into operable contact causes the absorber to come into operable contact with the second end of the chromatographic medium, causes the conductors to come into operable contact with the sample preparation zones, and causes the wash liquid applicator to come into operable contact with the labeled specific binding partner applicator that is located the farthest from the chromatographic medium.

13. The chromatographic assay device of claim 12 wherein at least one of the labeled specific binding partner applicators contains a labeled specific binding partner for the analyte in resolubilizable form.

14. The chromatographic assay device of claim 12 wherein the labeled specific binding partner applicator for receiving the sample contains a reagent for treatment of the sample before the sample is applied to the chromatographic medium.

15. The chromatographic assay device of claim 14 wherein the reagent is an extraction reagent for extracting analyte from the sample.

16. The chromatographic assay device of claim 13 wherein the labeled specific binding partner for the analyte is a visually detectable label.

17. The chromatographic assay device of claim 12 wherein the chromatographic medium further includes a control zone separate from the detection zone.

18. The chromatographic assay device of claim 17 wherein the control zone contains analyte immobilized thereto.

19. The chromatographic assay device of claim 12 wherein at least one of the first and second opposable components further includes an aperture for viewing of at least a portion of the chromatographic medium.

20. A test kit comprising, packaged in separate containers:
(a) the assay device of claim 12; and
(b) a wash liquid for application to the wash liquid applicator of the assay device.

21. A method for detecting and/or determining an analyte in a sample comprising the steps of:

(a) applying the sample to the labeled specific binding partner applicator located farthest from the chromatographic medium of the chromatographic assay device of claim 11;

(b) applying a wash liquid to the wash liquid applicator of the chromatographic assay device;

(c) bringing the first and second opposable components of the chromatographic assay device into operable contact;

(d) allowing the sample and the resolubilized labeled specific binding partner, followed by the wash liquid, to move through at least a portion of the chromatographic medium including the detection zone so the labeled specific binding partner gives a detectable indication of the present and/or quantity of the analyte; and (e) observing and/or measuring the labeled specific binding partner at the detection zone in order to detect and/or determine the analyte.

22. The method of claim 21 wherein the label of the labeled specific binding partner is a visually detectable label and the step of observing and/or measuring the labeled specific binding partner comprises visually observing the labeled specific binding partner.

23. A chromatographic assay device for detection and/or determination of an analyte comprising;

(a) a first opposable component including
   (i) a chromatographic medium having first and second ends and including a detection zone containing an immobilized specific binding partner for the analyte;
   (ii) a sample preparation zone for receiving a sample to be assayed, the sample preparation zone including a catalyst-labeled specific binding partner for the analyte in resolubilizable form, the sample preparation zone being separated from the chromatographic medium; and
   (iii) a first applicator containing a substance that participates in a reaction catalyzed by the catalyst to produce a detectable product, the first applicator being separated on the first opposable component from the chromatographic medium and the sample preparation zone; and (b) a second opposable component including:
   (i) a second applicator;
   (ii) a conductor; and (iii) an absorber separated from the conductor and the second applicator;

wherein the first and second opposable components are configured such that bringing the first and second opposable components into operable contact causes the second applicator to come into operable contact with both the first applicator and the sample preparation zone, causes the conductor to come into operable contact with both the sample preparation zone and the first end of the chromatographic medium, and causes the absorber to come into operable contact with the second end of the chromatographic medium.

24. The chromatographic assay device of claim 23 wherein the sample preparation zone contains at least one reagent for treatment of the sample before the sample is applied to the chromatographic medium.

25. The chromatographic assay device of claim 24 wherein the reagent is an extraction reagent for extracting analyte from the sample.

26. The chromatographic assay device of claim 23 wherein the catalyst is an enzyme.

27. The chromatographic assay device of claim 26 wherein the enzyme is selected from the group consisting of horseradish peroxidase, alkaline phosphatase, β-galactosidase, and glucose oxidase.

28. The chromatographic assay device of claim 23 wherein the substance that participates in a reaction is a substrate that is converted to an insoluble product that is deposited at the detection zone as the result of the action of the catalyst.

29. The chromatographic assay device of claim 23 wherein the chromatographic medium further includes a control zone separate from the detection zone.

30. The chromatographic assay device of claim 28 wherein the control zone includes analyte immobilized thereto.

31. The chromatographic assay device of claim 23 wherein at least one of the first and second opposable components further includes an aperture for viewing of at least a portion of the chromatographic medium.

32. A test kit, comprising, packaged in separate containers:
(a) the assay device of claim 23; and
(b) a wash liquid for application to the second applicator of the assay device.

33. A method for detecting and/or determining an analyte in a sample comprising the steps of:
(a) applying the sample to the sample preparation means of the chromatographic assay device of claim 23;
(b) applying a wash liquid to the second applicator of the chromatographic assay device;
(c) bringing the first and second opposable component into operable contact;
(d) allowing the sample and the reactant, followed by the wash liquid, to move through at least a portion of the chromatographic medium including the detection zone so that the labeled specific binding partner gives a detectable indication of the presence and/or quantity of the analyte; and
(e) observing and/or measuring the labeled specific binding partner at the detection zone in order to detect and/or determine the analyte.

34. A chromatographic assay device for detection and/or determination of an analyte in a sample comprising;
(a) a first opposable component including;
(i) a sample preparation zone containing a matrix of porous material permeable to the liquid portion of blood but capable of trapping the cellular components of blood;
(ii) a first applicator containing a labeled specific binding partner for the analyte in resolubilizable form in operable contact with the sample preparation zone; and
(iii) a chromatographic medium including a detection zone containing an immobilized specific binding partner for the analyte, the chromatographic medium being in operable contact with the first applicator, the chromatographic medium, first applicator, and sample preparation zone being so located that the first applicator is between the sample preparation zone and the chromatographic medium; and
(b) a second opposable component including:
(i) a second applicator; and
(ii) an absorber;

wherein the first and second opposable components are configured so that bringing the first and second opposable components into operable contact causes the second applicator to come into operable contact with the first applicator to apply a wash liquid thereto and causes the absorber to come into operable contact with the second end of the chromatographic medium.

35. The chromatographic assay device of claim 34 further comprising a barrier to prevent fluid flow between the second applicator and the sample preparation zone.

36. The chromatographic assay device of claim 34 wherein the chromatographic medium further includes a control zone separate from the detection zone.

37. The chromatographic assay device of claim 36 wherein the control zone includes analyte immobilized thereto.

38. A test kit comprising, packaged in separate containers:
(a) the assay device of claim 34; and
(b) a wash liquid for application to the second applicator of the assay device.

39. A method for detecting and/or determining an analyte in a test sample comprising the steps of:
(a) applying the test sample to the sample preparation zone of the chromatographic assay device of claim 34;
(b) applying a wash liquid to the second applicator of the chromatographic assay device;
(c) allowing the sample to migrate from the sample preparation zone through the first applicator to resolubilize the labeled specific binding partner and then through at least a portion of the chromatographic medium, the portion including the detection zone;
(d) bringing the first and second opposable components into operable contact to apply the wash liquid to the sample preparation zone and the first applicator;
(e) allowing the wash liquid to move through at least a portion of the chromatographic medium including the detection zone; and
(f) observing and/or measuring the labeled specific binding partner at the detection zone in order to detect and/or determine the analyte.

40. The method of claim 39 wherein the label of the labeled specific binding partner is a visually detectable label and the step of observing and/or measuring the labeled specific binding partner comprises visually observing the labeled specific binding partner.

41. A chromatographic assay device for detection and/or determination of at least one analyte comprising:
(a) a first opposable component including:

(i) a plurality of laterally separated sample preparation zones, each sample preparation zone for receiving a sample to be assayed; and (ii) a plurality of laterally separated chromatographic media, each chromatographic medium having first and second ends and including therein a detection zone containing an immobilized specific binding partner for an analyte, each chromatographic medium being located in a line with a sample preparation zone; and (b) a second opposable component including:
(i) a plurality of laterally separated conductors;
(ii) a plurality of laterally separated absorbers, each absorber being located in line with a conductor; and
(iii) a plurality of laterally separated applicators, each applicator being located in line with an absorber and a conductor;

wherein, when the first and second opposable components are brought into operable contact, each applicator is brought into operable contact with a corresponding sample preparation zone, each conductor is brought into operable contact with a corresponding sample preparation zone and with a corresponding chromatographic medium, and each absorber is brought into operable contact with the second end of a corresponding chromatographic medium.

42. The chromatographic assay device of claim 41 wherein at least one sample preparation zone includes a specific binding partner for an analyte in resolubilizable form.

43. The chromatographic assay device of claim 41 wherein at least one sample preparation zone includes a reagent for treatment of the sample before application of the sample to the chromatographic medium.

44. A chromatographic assay device for detection and/or determination of at least one analyte comprising:

(a) a first opposable component including:
(i) a plurality of laterally separated chromatographic media, each chromatographic medium having first and second ends and including thereon a detection zone containing an immobilized specific binding partner for an analyte;
(ii) for each chromatographic medium, a plurality of labeled specific binding partner applicators for applying a labeled specific binding partner for an analyte to the chromatographic medium, the labeled specific binding partner applicator located furthest from the chromatographic medium for receiving a sample to be assayed, each chromatographic medium being located on the first opposable component in line with an equal number of labeled specific binding partner applicators; and (b) a second opposable component including:
(i) a plurality of laterally-separated wash liquid applicators, one applicator for each chromatographic medium;
(ii) a plurality of laterally-separated conductors, each conductor being located in line with a wash liquid applicator, with there being at least as many conductors for each chromatographic medium as the number of labeled specific binding partner applicators minus one for each chromatographic medium; and
(iii) a plurality of laterally-separated absorbers, one absorber for each chromatographic medium, each absorber being located in line with a wash liquid applicator and a conductor;

wherein, when the first and second opposable components are brought into opposition, each wash liquid applicator is brought into operable contact with a corresponding labeled specific binding partner applicator, the corresponding labeled specific binding partner applicators being those that are located the farthest from each chromatographic medium, each conductor is brought into operable contact with either two corresponding labeled specific binding partner applicators or a corresponding labeled specific binding partner applicator and the first end of a corresponding chromatographic medium, and each absorber is brought into operable contact with the second end of a corresponding chromatographic medium.

45. The chromatographic assay device of claim 44 wherein at least one labeled specific binding partner applicator includes a labeled specific binding partner for an analyte in resolubilizable form.

46. The chromatographic assay device of claim 44 wherein at least one labeled specific binding partner applicator includes a reagent for treatment of the analyte.

47. A chromatographic assay device for detection and/or determination of at least one analyte comprising:

(a) a first opposable component including:
(i) a plurality of laterally-separated chromatographic media, each chromatographic medium having first and second ends and including thereon a detection zone containing an immobilized specific binding partner for an analyte;
(ii) a plurality of laterally-separated sample preparation zones, one for each chromatographic medium, each sample preparation zone including a specific binding partner for an analyte in a resolubilizable form labeled with a catalyst, each sample preparation zone being in line with a chromatographic medium; and
(iii) a plurality of first applicators, one for each chromatographic medium, each first applicator containing a substrate that participates in a reaction catalyzed by the catalyst, the reaction forming a detectable product, each first applicator being in line with a chromatographic medium and a sample preparation zone; and (b) a second opposable component including:
(i) a plurality of laterally-separated second applicators, one second applicator for each chromatographic medium;
(ii) a plurality of laterally-separated conductors, one conductor for each chromatographic medium, each conductor being in line with a second applicator; and
(iii) a plurality of laterally-separated absorbers, one absorber for each chromatographic medium, each absorber being in line with a second applicator and a conductor;

wherein the first and second opposable components are configured so that bringing the first and second opposable components into operable contact causes each second applicator to come into operable contact with a corresponding first applicator and sample preparation zone, causes each conductor to come into operable contact with a corresponding sample preparation zone and chromatographic medium via the first end of the chromatographic medium, and causes each absorber to come into operable contact with a corresponding chromatographic medium via the second end of each chromatographic medium.

48. The chromatographic assay device of claim 47 wherein the catalyst is an enzyme.

49. A chromatographic assay device for detection and/or determination of at least one analyte comprising:

(a) a first opposable component including:
(i) a plurality of laterally-separated chromatographic media, each chromatographic medium having first and second ends and including thereon a detection zone containing an immobilized specific binding partner for an analyte;
(ii) a plurality of laterally-separated first applicators, one first applicator for each chromatographic medium, each first applicator being in operable contact with the first end of a corresponding chromatographic medium; and
(iii) a plurality of laterally-separated sample preparation zones, each sample preparation zone being in operable contact with a corresponding first applicator, each sample preparation zone including therein a matrix of porous material permeable to the liquid portion of blood but capable of trapping the cellular components of blood; and (b) a second opposable component including:
(i) a plurality of laterally-separated second applicators, one for each chromatographic medium; and
(ii) a plurality of laterally-separated absorbers, one for each chromatographic medium, each absorber being in line with a second applicator;

wherein the first and second opposable components are configured so that bringing the first and second opposable components into operable contact causes each second applicator to come into operable contact with the corresponding first applicator and causes each absorber to come into operable contact with the corresponding chromatographic medium via the second end of the chromatographic medium.

50. The chromatographic assay device of claim 49 wherein each matrix of porous material contains a detergent and a chelating agent.

51. The chromatographic assay device of claim 34 wherein the matrix contains a detergent and a chelating agent.

* * * * *